US009497975B2

(12) United States Patent
Modak et al.

(10) Patent No.: US 9,497,975 B2
(45) Date of Patent: Nov. 22, 2016

(54) BROAD SPECTRUM NATURAL PRESERVATIVE COMPOSITION

(71) Applicant: The Trustees of Columbia University in the City of New York, New York, NY (US)

(72) Inventors: Shanta M. Modak, River Edge, NJ (US); Santoshkumar Hanmantrao Dongre, New York, NY (US); Nayana Baiju, Kochi (IN); Lauserpina A. Caraos, Hollis, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 14/294,933

(22) Filed: Jun. 3, 2014

(65) Prior Publication Data

US 2014/0287072 A1    Sep. 25, 2014

Related U.S. Application Data

(63) Continuation-in-part of application No. PCT/US2012/068107, filed on Dec. 6, 2012.

(60) Provisional application No. 61/567,372, filed on Dec. 6, 2011.

(51) Int. Cl.
| | |
|---|---|
| *A01N 65/00* | (2009.01) |
| *A01N 65/24* | (2009.01) |
| *A61Q 17/00* | (2006.01) |
| *A61K 8/34* | (2006.01) |
| *A61K 8/35* | (2006.01) |
| *A61K 8/92* | (2006.01) |
| *A61K 8/97* | (2006.01) |
| *A01N 31/04* | (2006.01) |
| *A01N 31/08* | (2006.01) |
| *A01N 31/16* | (2006.01) |
| *A01N 37/02* | (2006.01) |
| *A01N 65/06* | (2009.01) |
| *A01N 65/08* | (2009.01) |
| *A01N 65/44* | (2009.01) |

(52) U.S. Cl.
CPC ............ *A01N 65/24* (2013.01); *A01N 31/04* (2013.01); *A01N 31/08* (2013.01); *A01N 31/16* (2013.01); *A01N 37/02* (2013.01); *A01N 65/06* (2013.01); *A01N 65/08* (2013.01); *A01N 65/44* (2013.01); *A61K 8/34* (2013.01); *A61K 8/35* (2013.01); *A61K 8/922* (2013.01); *A61K 8/97* (2013.01); *A61Q 17/005* (2013.01)

(58) Field of Classification Search
CPC .................................................... A61K 36/00
USPC ......................................................... 424/725
See application file for complete search history.

(56) References Cited

U.S. PATENT DOCUMENTS

| | | | |
|---|---|---|---|
| 4,022,605 | A | 5/1977 | Konya et al. |
| 4,049,802 | A | 9/1977 | Fox, Jr. |
| 4,330,531 | A | 5/1982 | Alliger |
| 4,404,197 | A | 9/1983 | Fox, Jr. et al. |
| 4,563,485 | A | 1/1986 | Fox, Jr. et al. |
| 4,579,731 | A | 4/1986 | Fox, Jr. et al. |
| 4,581,028 | A | 4/1986 | Fox, Jr. et al. |
| 4,612,337 | A | 9/1986 | Fox, Jr. et al. |
| 4,723,950 | A | 2/1988 | Lee |
| 4,859,359 | A | 8/1989 | DeMatteo et al. |
| 4,867,898 | A | 9/1989 | Spaulding et al. |
| 4,956,354 | A | 9/1990 | Gutierrez |
| 4,975,217 | A | 12/1990 | Brown-Skrobot et al. |
| 5,019,096 | A | 5/1991 | Fox, Jr. et al. |
| 5,033,488 | A | 7/1991 | Curtis et al. |
| 5,073,366 | A | 12/1991 | Beck |
| 5,091,442 | A | 2/1992 | Milner |
| 5,100,652 | A | 3/1992 | Kross et al. |
| 5,135,747 | A | 8/1992 | Faryniarz et al. |
| 5,180,605 | A | 1/1993 | Milner |
| 5,200,194 | A | 4/1993 | Edgren et al. |
| 5,209,251 | A | 5/1993 | Curtis et al. |
| 5,261,421 | A | 11/1993 | Milner |
| 5,310,546 | A | 5/1994 | Douglas |
| 5,334,588 | A | 8/1994 | Fox, Jr. et al. |
| 5,567,495 | A | 10/1996 | Modak et al. |
| 5,614,538 | A | 3/1997 | Nelson, Jr. |

(Continued)

FOREIGN PATENT DOCUMENTS

| | | |
|---|---|---|
| CH | 654327 | 2/1986 |
| DE | DE 202008002718 U1 | 7/2009 |

(Continued)

OTHER PUBLICATIONS

Tayyem et al., Nutrition and Cancer, 55(2), 126-131, 2006.*

(Continued)

*Primary Examiner* — Michael Meller
(74) *Attorney, Agent, or Firm* — Baker Botts L.L.P.

(57) ABSTRACT

Disclosed herein are preservative compositions comprising effective amounts of an alcohol, such as benzyl alcohol ("BA"), ethyl alcohol or phenyl ethanol, and cinnamon bark oil ("CB"), cinnamaldehyde ("CMA"), thyme oil, thymol, galangal oil, botanical extracts or combinations thereof, each of which are preferably obtained from natural sources. These preservatives have been observed to show broad spectrum anti microbial efficacy in both anionic and cationic formulations. In certain non-limiting embodiments, such compositions further comprise tetrahydrocurcuminoid ("THC"), phenyl ethanol and/or orange oil ("OR") or rosemary oil ("RM").

2 Claims, No Drawings

(56) References Cited

U.S. PATENT DOCUMENTS

| | | |
|---|---|---|
| 5,616,338 A | 4/1997 | Fox, Jr. et al. |
| 5,772,640 A | 6/1998 | Modak et al. |
| 5,854,266 A | 12/1998 | Nelson, Jr. |
| 5,866,527 A * | 2/1999 | Mertens .................. C11D 3/50 510/365 |
| 5,891,422 A | 4/1999 | Pan et al. |
| 5,968,539 A | 10/1999 | Beerse et al. |
| 5,985,819 A | 11/1999 | Lu et al. |
| 5,985,918 A | 11/1999 | Modak et al. |
| 6,075,056 A | 6/2000 | Quigley, Jr. et al. |
| 6,083,208 A | 7/2000 | Modak et al. |
| 6,106,505 A | 8/2000 | Modak et al. |
| 6,120,758 A | 9/2000 | Siddiqui et al. |
| 6,270,811 B1 | 8/2001 | Fregonese |
| 6,280,758 B1 | 8/2001 | Warren et al. |
| 6,287,583 B1 | 9/2001 | Warren et al. |
| 6,312,675 B1 | 11/2001 | Deane |
| 6,319,958 B1 | 11/2001 | Johnson et al. |
| 6,323,166 B1 | 11/2001 | Kamiya |
| 6,348,501 B1 | 2/2002 | Holt et al. |
| 6,397,224 B1 | 5/2002 | Zubeldia et al. |
| 6,420,326 B1 | 7/2002 | Maile et al. |
| 6,451,748 B1 | 9/2002 | Taylor et al. |
| 6,537,955 B1 | 3/2003 | Raso et al. |
| 6,582,719 B2 | 6/2003 | Modak et al. |
| 6,616,922 B2 | 9/2003 | Taylor et al. |
| 6,630,163 B1 | 10/2003 | Murad |
| 6,632,784 B2 | 10/2003 | Massaux et al. |
| 6,696,399 B1 | 2/2004 | Chernin et al. |
| 6,699,825 B2 | 3/2004 | Rees et al. |
| 6,716,883 B1 | 4/2004 | Casper et al. |
| 6,753,305 B2 | 6/2004 | Raso et al. |
| 6,858,317 B2 | 2/2005 | Aamodt et al. |
| 6,921,745 B2 | 7/2005 | Yamada et al. |
| 6,951,833 B2 | 10/2005 | O'Neil |
| 6,969,522 B2 | 11/2005 | Bessette et al. |
| 6,974,584 B2 | 12/2005 | Bessette |
| 7,247,295 B2 | 7/2007 | Schmaus et al. |
| 7,435,429 B2 | 10/2008 | Modak et al. |
| 7,563,461 B2 | 7/2009 | Modak et al. |
| 7,572,469 B2 | 8/2009 | Santo et al. |
| 7,745,425 B2 | 6/2010 | Modak et al. |
| 7,871,649 B2 | 1/2011 | Modak et al. |
| 7,985,773 B2 | 7/2011 | Greten et al. |
| 2001/0010016 A1 | 7/2001 | Modak et al. |
| 2001/0024661 A1 | 9/2001 | Modak et al. |
| 2002/0122876 A1 | 9/2002 | Modak et al. |
| 2002/0165130 A1 | 11/2002 | Johnson et al. |
| 2002/0173775 A1 | 11/2002 | Modak et al. |
| 2002/0192256 A1 | 12/2002 | Wu et al. |
| 2003/0113388 A1 | 6/2003 | Phan |
| 2003/0168077 A1 | 9/2003 | Brown et al. |
| 2003/0180233 A1 | 9/2003 | Anderson et al. |
| 2003/0213168 A1 | 11/2003 | Hesse et al. |
| 2004/0092482 A1 | 5/2004 | Gupta |
| 2004/0102429 A1 | 5/2004 | Modak et al. |
| 2004/0132667 A1 | 7/2004 | Lintner |
| 2004/0192551 A1 | 9/2004 | Bessette et al. |
| 2004/0247685 A1 | 12/2004 | Modak et al. |
| 2004/0253275 A1 | 12/2004 | Eini et al. |
| 2005/0026802 A1 | 2/2005 | Kilkenny et al. |
| 2005/0048139 A1 | 3/2005 | Modak et al. |
| 2005/0187124 A1 * | 8/2005 | Li ....................... C11D 3/0031 510/278 |
| 2005/0222276 A1 | 10/2005 | Schmaus et al. |
| 2005/0238602 A1 | 10/2005 | Modak et al. |
| 2006/0018867 A1 | 1/2006 | Kawasaki et al. |
| 2006/0051384 A1 | 3/2006 | Scholz et al. |
| 2006/0099237 A1 | 5/2006 | Modak et al. |
| 2006/0198800 A1 | 9/2006 | Dilallo et al. |
| 2006/0216246 A1 | 9/2006 | Belanger et al. |
| 2006/0233901 A1 | 10/2006 | Jamieson et al. |
| 2006/0293201 A1 | 12/2006 | Simon et al. |
| 2006/0293214 A1 | 12/2006 | Cheng et al. |
| 2007/0003538 A1 | 1/2007 | Madhyastha |
| 2007/0014823 A1 | 1/2007 | Iwata et al. |
| 2007/0020342 A1 | 1/2007 | Modak et al. |
| 2007/0027119 A1 | 2/2007 | Ahmed et al. |
| 2007/0190094 A1 | 8/2007 | Bessette et al. |
| 2007/0275070 A1 | 11/2007 | Ahmed et al. |
| 2007/0286813 A1 | 12/2007 | Toutounghi |
| 2008/0008729 A1 | 1/2008 | Swaine et al. |
| 2008/0038219 A1 | 2/2008 | Mosbaugh et al. |
| 2008/0063607 A1 | 3/2008 | Tamarkin et al. |
| 2008/0166314 A1 | 7/2008 | Jochim et al. |
| 2008/0226568 A1 | 9/2008 | Rozsa et al. |
| 2008/0234173 A1 | 9/2008 | Warr et al. |
| 2008/0253976 A1 | 10/2008 | Scott et al. |
| 2008/0260708 A1 | 10/2008 | Hall |
| 2008/0299220 A1 | 12/2008 | Tamarkin et al. |
| 2008/0311231 A1 | 12/2008 | Modak et al. |
| 2008/0317737 A1 | 12/2008 | Patel et al. |
| 2008/0318784 A1 | 12/2008 | Koo et al. |
| 2009/0004122 A1 | 1/2009 | Modak et al. |
| 2009/0028751 A1 | 1/2009 | Robbins |
| 2009/0029961 A1 | 1/2009 | Modak et al. |
| 2009/0035228 A1 | 2/2009 | Modak et al. |
| 2009/0068255 A1 | 3/2009 | Yu et al. |
| 2009/0088358 A1 | 4/2009 | Roso et al. |
| 2009/0165812 A1 | 7/2009 | Resnick et al. |
| 2009/0175806 A1 | 7/2009 | Modak et al. |
| 2009/0191288 A1 | 7/2009 | Squires et al. |
| 2009/0300864 A1 | 12/2009 | Adkins et al. |
| 2010/0034871 A1 | 2/2010 | Mikkelsen et al. |
| 2010/0140368 A1 | 6/2010 | De Lame et al. |
| 2010/0172847 A1 | 7/2010 | Modak et al. |
| 2010/0172848 A1 | 7/2010 | Modak et al. |
| 2010/0183524 A1 | 7/2010 | Zielinski et al. |
| 2010/0196494 A1 | 8/2010 | Van Beek |
| 2010/0216889 A1 | 8/2010 | Modak et al. |
| 2010/0234460 A1 | 9/2010 | Foret et al. |
| 2010/0248962 A1 | 9/2010 | Wilczynski et al. |
| 2010/0317743 A1 | 12/2010 | Macinga et al. |
| 2010/0323043 A1 | 12/2010 | Perla et al. |
| 2011/0028563 A1 | 2/2011 | Found |
| 2011/0070316 A1 | 3/2011 | Modak et al. |
| 2011/0070376 A1 | 3/2011 | Wales et al. |
| 2011/0142899 A1 | 6/2011 | Lagaron Abello et al. |
| 2012/0100231 A1 | 4/2012 | Perla et al. |
| 2012/0129950 A1 | 5/2012 | Macinga et al. |
| 2012/0171156 A1 | 7/2012 | Basketter et al. |
| 2012/0201902 A1 | 8/2012 | Modak et al. |
| 2012/0207862 A1 | 8/2012 | Morre et al. |
| 2013/0230609 A1 | 9/2013 | Modak et al. |
| 2014/0079819 A1 | 3/2014 | Debaun et al. |
| 2014/0178447 A1 | 6/2014 | Modak et al. |
| 2014/0242198 A1 | 8/2014 | Modak et al. |
| 2014/0243417 A1 | 8/2014 | Modak et al. |
| 2014/0322147 A1 | 10/2014 | Modak et al. |
| 2015/0265666 A1 | 9/2015 | Modak et al. |

FOREIGN PATENT DOCUMENTS

| | | |
|---|---|---|
| EP | 0 054 205 | 6/1982 |
| EP | 0 106 266 | 4/1984 |
| EP | 1108419 | 6/2001 |
| EP | 1 146 112 | 10/2001 |
| EP | 1206933 | 5/2002 |
| EP | 1 288 285 | 3/2003 |
| FR | 2771632 | 6/1999 |
| FR | 2874928 | 3/2010 |
| GB | 1 060 447 | 3/1967 |
| JP | 1997-323910 | 12/1997 |
| JP | 2002-193717 | 7/2002 |
| JP | 2002-370958 | 12/2002 |
| JP | 2004-217615 | 8/2004 |
| JP | 04250331 | 9/2004 |
| JP | 2004277554 | 10/2004 |
| JP | 2004-322078 | 11/2004 |
| JP | 2006-225289 | 8/2006 |
| JP | 2007-291049 | 11/2007 |
| JP | 2010-083806 | 4/2010 |
| JP | 2010-184987 | 8/2010 |
| KR | 10-2004-077206 | 9/2004 |

(56) References Cited

FOREIGN PATENT DOCUMENTS

| | | |
|---|---|---|
| SU | 513676 | 5/1976 |
| WO | WO 84/04556 | 11/1984 |
| WO | WO 85/01208 | 3/1985 |
| WO | WO 89/06962 | 8/1989 |
| WO | WO 92/04029 | 3/1992 |
| WO | WO 93/02717 | 2/1993 |
| WO | WO 98/51273 | 11/1998 |
| WO | WO 99/22718 | 5/1999 |
| WO | WO 00/65011 | 11/2000 |
| WO | WO 01/72262 | 10/2001 |
| WO | WO 01/91555 | 12/2001 |
| WO | WO 02/22060 | 3/2002 |
| WO | WO 03/000303 | 1/2003 |
| WO | WO 03/018498 | 3/2003 |
| WO | WO 03/018743 | 3/2003 |
| WO | WO 03/077856 | 9/2003 |
| WO | WO 03/078367 | 9/2003 |
| WO | WO 2004/004631 | 1/2004 |
| WO | WO 2004/014416 | 2/2004 |
| WO | WO 2006/010269 | 2/2006 |
| WO | WO 2006/023349 | 3/2006 |
| WO | WO 2006/099359 | 9/2006 |
| WO | WO 2007/069214 | 6/2007 |
| WO | WO 2007/071089 | 6/2007 |
| WO | WO 2007/077573 | 7/2007 |
| WO | WO 2007/095041 | 8/2007 |
| WO | WO 2007/101848 | 9/2007 |
| WO | WO 2007/123790 | 11/2007 |
| WO | WO 2007/126651 | 11/2007 |
| WO | WO 2008/031087 | 3/2008 |
| WO | WO 2008/042197 | 4/2008 |
| WO | WO 2008/061187 | 5/2008 |
| WO | WO 2008/119841 | 10/2008 |
| WO | WO 2008/154395 | 12/2008 |
| WO | WO 2008/157847 | 12/2008 |
| WO | WO 2009/062746 | 3/2009 |
| WO | WO 2009/049208 | 4/2009 |
| WO | WO 2010/091415 | 8/2010 |
| WO | WO 2010/119369 | 10/2010 |
| WO | WO 2011/002929 | 1/2011 |
| WO | WO 2011/151835 | 12/2011 |
| WO | WO 2012/017349 | 2/2012 |
| WO | WO 2012/051204 | 4/2012 |
| WO | WO 2014/092999 | 6/2014 |

OTHER PUBLICATIONS

M. Segvic Klaric et al., 2006, The Society for Applied Microbiology, Letters in Applied Microbiology 44 (2007) 36-42.*
U.S. Appl. No. 12/134,918, Apr. 22, 2015 Non Final Office Action.
U.S. Appl. No. 12/694,119, May 8, 2015 Final Office Action.
U.S. Appl. No. 12/016,788, Mar. 6, 2015 Non-Final Office Action.
U.S. Appl. No. 12/016,788, Jun. 2, 2015 Response to Non-Final Office Action.
Baratta, et al., "Antimicrobial and antioxidant properties of some commercial essential oils", Flavour Fragr. J., 13,235±244 (1998).
Biosource Naturals, product sheet for Lemongrass oil. Downloaded Apr. 5, 2015, from http://www.biosourcenaturals.com/lemongrass-essential.oil.htm.
Fact Sheet on Basil oil from Chemical Book, Downloaded Apr. 5, 2015, from http://www.chemicalbook.com/ChemicalProductProperty_US_CB3405198.aspx.
Prabuseenivasan, et al., "In vitro antibacterial activity of some plant essential oils", BMC Complementary and Alternative Medicine 2006, 6:39, pp. 1-8.
Skin Care, retrieved from URL:<https://web.archive.org/web/20050119140921/http://www.morganics.com/store/page8.html> , Jan. 19, 2005.
Subba, et al., "Antimicrobial Action of Citrus Oils" J. Food Sci. 1967, vol. 32, pp. 225-227.
Wilson, et al., "The quantification of citral in lemongrass and lemon oils by near-infrared spectroscopy", Journal of Pharmacy and Pharmacology 2002, 54: 1257-1263.
U.S. Appl. No. 12/016,788, Oct. 22, 2015 Final Office Action.
U.S. Appl. No. 12/134,911, Sep. 8, 2014 Notice of Allowance.
U.S. Appl. No. 12/134,911, Dec. 8, 2014 Issue Fee Payment.
U.S. Appl. No. 12/134,918, Jul. 31, 2015 Response to Non-Final Office Action.
U.S. Appl. No. 12/134,918, Nov. 4, 2015 Final Office Action.
U.S. Appl. No. 13/335,363, Jul. 8, 2015 Non-Final Office Action.
U.S. Appl. No. 13/412,464, Jun. 22, 2015 Final Office Action.
"Lemongrass Oil: Lighten Up Your Mood with This All-Around Oil", Herbal Oil: Lemongrass Oil Benefits and Uses, 4 pages, 2015, http://articles.mercola.com/herbal-oils/lemongrass-oil.aspx.
Anand, et al., "Biological activities of curcumin and its analogues (Congeners) made by man and Mother Nature" Biochemical Pharmacology, 2008, vol. 76, pp. 1590-1611.
Bagamboula, et al., "Inhibitory effect of thyme and basil essential oils, carvacrol, thymol, estragol, linalool and p-cymene towards Shigella sonnei and S. flexneri" Food Microbiology 21 (2004) 33-42.
Chalchat, et al., Chemical Composition of Essential Oil of *Calendula oficinalis* L. (Pot Marigold), Flavour and Fragrance Journal, vol. 6, 189-192 (1991).
Chang, et al., Resources and bioactive substances from Taiwania (*Taiwania cryptomerioides*). J. Wood Sci (2003) 49:1-4.
Collins, et al., "A review of alternatitves to organophosphorus compounds for the control of storage mites", Journal of Stored Products Research, vol. 42, No. 4, Jan. 1, 2006, pp. 395-426, XP028024314.
DailyMed Antiseptic skin cleanser—Chlorhexidine gluconate, Drug Label Information, updated Sep. 2012.
Nerio, et al., "Repellant activity of essential oils: A review", Biosource Technology, vol. 101, No. 1, Jan. 1, 2010, pp. 372-378, XP026624017.
Panchatcharam, et al., "Curcumin improves wound healing by modulating collagen and decreasing reactive oxygen species". Molecular and Cellular Biochemistry, vol. 290, No. 1-2, Jun. 13, 2006, pp. 87-95, XP019436632.
Reagor, et al., "The Effectiveness of Processed Grapefruit-Seed Extract as an Antibacterial Agent: 1. An in Vitro Agar Assay" The Journal of Alternative and Complementary Medicine, 2002, vol. 8, pp. 325-332.
Supplementary Partial European Search Report dated Aug. 12, 2015 in Application No. 12840062.3.
Table of Acids with Ka and pKa, Downloaded Sep. 28 from the site: Downloaded Sep. 28, 2015, from http://clas.sa.ucsb.edu/staff/Resource%20folder/Chem109ABC/Acid,%20Base%20Strength/Table%20of%20Acids%20w%20Kas%20and%20pKas.pdf.
Zeus Quicmica, "Zemea Propanediol", Information sheet, downloaded Jun. 24, 2015.
U.S. Appl. No. 12/694,119, Nov. 5, 2015 Amendment and Request for Continued Examination (RCE).
U.S. Appl. No. 13/412,464, Sep. 11, 2015 Notice of Appeal Filed.
U.S. Appl. No. 14/194,381, Jan. 4, 2016 Non-Final Office Action.
U.S. Appl. No. 14/267,403, Nov. 17, 2015 Non-Final Office Action.
U.S. Appl. No. 12/694,119, Feb. 2, 2016 Applicant Initiated Interview Summary.
U.S. Appl. No. 12/694,119, Jan. 20, 2016 Non-Final Office Action.
U.S. Appl. No. 14/267,606, Jan. 29, 2016 Non-Final Office Action.
Tecophilic TPU—LifeScience Polymers—The Lubrizol Corporation; "Tecophilic TPU"; https://web.archive.org/web/20140923074123/http://www.lubrizol.com/LifeScience/Products/Tecophilic.html; Sep. 23, 2014 [downloaded from internet Jan. 12, 2016]: entire document.
U.S. Appl. No. 12/016,788, Jun. 2, 2016 Notice of Abandonment.
U.S. Appl. No. 12/134,918, Apr. 4, 2016 Amendment and Request for Continued Examination (RCE).
U.S. Appl. No. 12/367,851, Feb. 5, 2010 Notice of Abandonment.
U.S. Appl. No. 12/694,141, Mar. 1, 2013 Notice of Abandonment.
U.S. Appl. No. 13/335,363, Feb. 9, 2016 Notice of Abandonment.
U.S. Appl. No. 13/412,464, May 9, 2016 Notice of Abandonment.
U.S. Appl. No. 14/267,403, Mar. 17, 2016 Response to Non-Final Office Action.
U.S. Appl. No. 14/267,403, Apr. 27, 2010 Response to Non-Final Office Action.

(56) References Cited

OTHER PUBLICATIONS

U.S. Appl. No. 14/267,606, Apr. 27, 2016 Response to Non-Final Office Action.
U.S. Appl. No. 14/564,920, filed Dec. 9, 2014.
U.S. Appl. No. 12/016,788, Dec. 18, 2014 Amendment and Request for Continued Examination.
U.S. Appl. No. 12/134,918, Jan. 26, 2015 Amendment and Request for Continued Examination.
U.S. Appl. No. 12/134,918, Apr. 22, 2015 Non-Final Office Action.
U.S. Appl. No. 12/694,119, Dec. 18, 2014 Response to Non-Final Office Action.
U.S. Appl. No. 13/412,464, Feb. 17, 2015 Amendment and Request for Continued.
U.S. Appl. No. 13/412,464, Apr. 20, 2015 Non-Final Office Action.
U.S. Appl. No. 13/412,464, Jun. 8, 2015 Response to Non-Final Office Action.
U.S. Appl. No. 13/335,363, Dec. 18, 2014 Response to Non-Final Office Action.
U.S. Appl. No. 13/335,363, Mar. 4, 2015 Final Office Action.
U.S. Appl. No. 13/335,363, Apr. 28, 2015 Amendment and Request for Continued Examination.
EP Office Action dated Dec. 2, 2014 in EP Application No. 10 794 733.5.
U.S. Appl. No. 12/134,918, Aug. 28, 2014 Final Office Action.
U.S. Appl. No. 13/335,363, Sep. 2, 2014, Non-Final Office Action.
U.S. Appl. No. 13/412,464, Oct. 17, 2014 Final Office Action.
U.S. Appl. No. 13/335,363, Sep. 2, 2014 Non-Final Office Action.
Khazaain-al-Advia vol. III (20th century AD), Mohammad Najmul Ghani Khan, Nadeem Yunus Printer/Sheikh Mohd Basheer & Sons, Lahore, 1926 AD p. 1050.
Qaraabaadeen Najm-al-Ghani (20th century AD), Mohammad Najmul Ghani Khan, Munshi Nawal Kishore, Lucknow, (Second Edition) 1928 AD p. 492.
Khazaain-al-Advia vol. II (20th century AD), Mohammad Najmul Ghani Khan, Nadeem Yunus Printer/Sheikh Mohd Basheer & Sons, Lahore, 1911 AD p. 657.
Kitaab-al-Umdah-fil-Jeraahat, Part I (13th century AD), Aminuddaulah Abul Farj Ibn Al-Quff Maseehi; Dayerah-al-Ma'aarif Usmania, Hyberabad, 1947 AD p. 234-235.
Ziya Al-Din Abdullah Ibn Al-Baiter; al Jaam'e-li-Mufradaat-al-Advia-wal-Aghzia, vol. II (13th century AD), Matba Amra, Cairo, Egypt, 1874 AD p. 84.
Sodhalanighantauh—(Namasamgraha Va Gunasamgraha) Sodhala; Edited by P.V. Sharma, Oriental Institute, Broda, Edn $1^{st}$ 1978 p. 116.
Khazaain-al-Advia vol. II (20th century AD), Mohammad Najmul Ghani Khan, Nadeem Yunus Printer/Sheikh Mohd Basheer & Sons, Lahore, 1911 AD p. 342-343.
Kitaab-al-Haawi-fil-Tibb, vol. IX (9th century AD), ABU Bakr Mohammad Bin Zakariyya Al-Razi: Dayerah-al-Ma'aarif Usmania, Hyberabad, (First Edition) 1960 AD p. 194.
Khazaain-al-Advia, vol. I ($20^{th}$ century AD) Mohammad Najmul Ghani Khan; Nadeem Yunus Printer/Sheikh Mohd Basheer & Sons, Lahore, 1911 AD p. 669.
Vagabhata; Astanga Hrdaya—(commentary by Arunadutta) edited by Bhisagacarya Harisastri Paradakara Vaidya; Chaukhamba Orientalia, Varanasi, edn. $8^{th}$, 1998 [Time of origin $5^{th}$ century]; p. 890.
Mohammad Azam Khan; Muheet-e-Azam, vol. I ($19^{th}$ century AD), Matba Nizami, Kanpur, 1896 AD p. 197.
International Search Report and Written Opinion for PCT/US14/29486, dated Oct. 10, 2014.
Biosecur Lad Inc., "Biosecur™ Product Line Recieves Self-Affirmed Gras Status for Use as an antioxidant and Nutrient Supplement", Biosecur News Release 030811, Mar. 10, 2011, (2 pages).
Hazan et al., "Benzoic Acis, a Weak Organic Acid Food Preservative, Exerts specific Effects on Intracellular Membrane Trafficking Pathways in *Saccharomyces cerevisiae*", Appl. Environ. Microbiol., 70(8):4449 (2004).

Song, et al., "Volatiles from Ficus hispida and their attractiveness to fig wasps", Journal of Chemical Ecology, 27;1929-1942 (2001).
Komthong et al., "Ascending bubble extraction of terpenes from freshly squeezed orange juice", Food Research International, 39;53-58 (2006).
Kumar et al., "Assessment of *Thymus vulgaris* L. essential oil as a safe botanical preservative against post harvest fungal infestation of food commodities", Innovative Food Service & Emerging Technologies, 9(4):575-580 (Oct. 2008).
Gemeda et al., "Effect of essential oils on aspergillus spore germination, growth and mycotoxin production: a potential source of botanical food preservative", APJTB, 4(Suppl. 1):S373-381 (May 2014).
U.S. Appl. No. 12/367,851, filed Feb. 9, 2009, (Abandoned).
U.S. Appl. No. 12/136,530, filed Jun. 10, 2008, (Abandoned).
U.S. Appl. No. 14/267,606, filed May 1, 2014.
U.S. Appl. No. 14/267,403, filed May 1, 2014.
U.S. Appl. No. 12/694,119, Dec. 21, 2012 Amendment and Request for Continued Examination (RCE).
U.S. Appl. No. 12/694,119, Jun. 22, 2012 Final Office Action.
U.S. Appl. No. 12/694,119, Jan. 12, 2012 Response to Non-Final Office Action.
U.S. Appl. No. 12/694,119, Oct. 12, 2012 Non-Final Office Action.
U.S. Appl. No. 12/016,788, Aug. 24, 2012 Final Office Action.
U.S. Appl. No. 12/016,788, Apr. 24, 2012 Response to Non-Final Office Action.
U.S. Appl. No. 12/016,788, Oct. 24, 2012 Non-Final Office Action.
U.S. Appl. No. 12/134,918, Jan. 31, 2013 Amendment and Request for Continued Examination (RCE).
U.S. Appl. No. 12/134,918, Jul. 31, 2012 Final Office Action.
U.S. Appl. No. 12/134,918, Mar. 28, 20102 Response to Non-Final Office Action.
U.S. Appl. No. 12/134,918, Nov. 15, 2011 Non-Final Office Action.
U.S. Appl. No. 12/694,141, Jul. 24, 2012 Final Office Action.
U.S. Appl. No. 12/694,141, Mar. 28, 2012 Response to Non-Final Office Action.
U.S. Appl. No. 12/694,141, Nov. 28, 2011 Non-Final Office Action.
U.S. Appl. No. 12/134,911, May 2, 2012 Amendment and Request for Continued Examination (RCE).
U.S. Appl. No. 12/134,911, Dec. 2, 2011, Final Office Action.
U.S. Appl. No. 12/134,911, Aug. 18, 2011 Response to Non-Final Office.
U.S. Appl. No. 12/134,911, Feb. 18, 2011 Non-Final Office Action.
U.S. Appl. No. 12/136,530, Feb. 1, 2012 Notice of Abandonment.
U.S. Appl. No. 12/135,530, Jun. 29, 2011 Non-Final Office Action.
U.S. Appl. No. 13/335,363, Feb. 19, 2013 Non-Final Office Action.
U.S. Appl. No. 12/016,788, Feb. 22, 2013 Amendment and Request for Continued Examination (RCE).
U.S. Appl. No. 12/016,788, Aug. 1, 2013 Non-Final Office Action.
U.S. Appl. No. 13/335,363, Nov. 1, 2013 Final Office Action.
U.S. Appl. No. 13/335,363, Aug. 15, 2013 Response to Non-Final Office Action.
U.S. Appl. No. 12/134,918, Nov. 7, 2013 Non-Final Office Action.
U.S. Appl. No. 12/694,119, Jun. 26, 2014 Non-Final Office Action.
U.S. Appl. No. 12/016,788, Jun. 19, 2014 Final Office Action.
U.S. Appl. No. 13/335,363, Apr. 1, 2014 Amendment and Request for Continued Examination (RCE).
U.S. Appl. No. 13/412,464, Jul. 7, 2014 Response to Non-Final Office Action.
U.S. Appl. No. 12/134,918, May 7, 2014 Response to Non-Final Office Action.
U.S. Appl. No. 12/136,560, filed Jun. 10, 2008, (Abandoned).
U.S. Appl. No. 12/134,911, May 2, 2012, Amendment and Request for Continued Examination (RCE).
U.S. Appl. No. 12/134,911, Dec. 2, 2011 Final Office Action.
U.S. Appl. No. 12/134,911, Aug. 18, 2011 Response to Non-Final Office Action.
U.S. Appl. No. 12/134,911, Feb. 18, 2011 Non Final Office Action.
U.S. Appl. No. 12/136,530, Jun. 29, 2011 Non-Final Office Action.
Entry for "citral" in Merck Index, 14th Edition.
Entry for Lemongrass oil, downloaded Jul. 15, 2012 from internet site: https://www.essentialoils.co.za/essential-oils/lemongrass.htm.

(56) References Cited

OTHER PUBLICATIONS

Entry for Orange Oil, downloaded Jul. 15, 2012 from internet site: https://www.essentialoils.co.za/essential-oils/orange.htm.
Judžentiené, et al., "Characteristics of essential oil composition in the needles of young Scots pine (*Pinus sylvestris* L.) stands growing along an aerial ammonia gradient", *Chemija*, 17(4):67-73, 2006.
Kurita, et al., "Synergistic Antimicrobial Effect of Ethanol, Sodium Chloride, Acetic Acid and Essential Oil Components", *Agricultural Biology Chemistry*, 47(1):67-75, 1983.
Mohammad Najmul Ghani Khan; Khazaain-al-Advia, vol. II (20th century AD), Nadeem Yunus Printer/Sheikh Mohd Basheer & Sons, Lahore, 1911 AD p. 656.
Mohammad Najmul Ghani Khan; Qaraabaadeen Najm-al-Ghani (20th century AD), Munshi Nawal Kishore, Lucknow, (Second Edition) 1928 AD p. 566.
Mohammad Azam Khan; Muheet Azam vol. II (Part II) (19th century AD), Matba Nizami, Kanpur, 1898 AD p. 3.
Susruta; Susruta Samhita—Edited & translated by P.V. Sharma, vol. III: Chaukhamba Visvabharati, Varanasi, Edn. 1st, 2001. [Time of origin 1000 BC—5th century] p. 10.
Mohammad Azam Khan; Muheet-e-Azam vol. III (19th century AD), Matba Nizami, Kanpur, 1887 AD p. 261.
Mohammad Shareef Khan; Ilaaj-al-Amraaz (18th centruy AD), Afzal-al-Matabe, Barqi Press, Delhi, 1921 AD p. 357.
Siddhayogasamgrahah—Compiled Yadavji Trikamji Acharya, Sri Baidyanath Ayurved Bhawan, Allahabad, Edn. 1st 1978 pp. 131-132.
Mohammad Najmul Ghani Khan; Khazaain-al-Advia, vol. III (20th century AD), Nadeem Yunus Printer/Sheikh Mohd Basheer & Sons, Lahore, 1926 AD p. 568.
Sarngadharacarya; Saringadhara Samhita—Translated by Smt. Shailaja Srivastava: Chaukhamba Orientalia, Varansai, Edn. 2nd, 1998. [Time of origin 13th century] pp. 431-432.
Ziya Al-Din Abdullah Ibn Al-Baitar; Al-Jaam'e-li-Mufradaat-al-Advia-wal-Aghzia, vol. IV (13th century AD), Matba Amra, Cario, Egypt, 1874 AD p. 57.
Abu Bakr Mohammad, Bin Zakariyya Al-Razi; Kitaab-al-Haawifil-Tibb, vol. II (9th century AD), Dayerah-Al-Ma'aarof Is,amoa. Juderabad, 1976 AD p. 434.
Mohammad Shareef Khan; Ilaaj-al-Amraaz (18th centruy AD), Afzal-al-Matabe, Barqi Press, Delhi, 1921 AD p. 335.
Mohammad Azam Khan; Maheet-e-Azam vol. III (19th century AD), Matba Nizami, Kanpur, 1887 AD p. 69.
Mohammad Najmul Ghani Khan; Khazaain-al-Advia, vol. II (20th century AD), Nadeem Yunus Printer/Sheikh Mohd Basheer & Sons, Lahore, 1911 AD p. 657.
Mohammad Azam Khan; Mulleet-e-Azam vol. III (19th century AD), Matba Nizami, Kanpur, 1887 AD p. 261.
Mohammad Azam Khan; Muheet-e-Azam vol. I (19th century AD), Matba Nizami, Kanpur, 1896 AD p. 257.
Cakrapanidattah; Cakradattah—Translated by Indradeva Tripathi; Chaukhamba Sanskrit Samsthan (Varanasi), Ed. 4th 2002, p. 260.
Baiju, et al., "Development of a Novel Surface Disinfectant Composition Containing Essential Oils and Fruit Acid Against Nosocomial Pathogens Commonly Associated with Environmental Surfaces", *International Journal of Essential Oil Therapeutics*, vol. 2:9-14 (2008).
Bezic, et al., "Composition and antimicrobial activity of *Achillea clavennae* L. essential oil." *Phytother. Res.* 19(9):1037-1040 (2003).
Bion, 2008, "Acne Treatment Products" http://www.bion-research.com/acne_treatment_products.htm.
Bion, 2008, "Moderate to Severe Acne" http://www.bion-research.com/moderate_to_severe_acne.htm.
Brehm-Stecher et al., "Sensitization of *Staphylococcus aureus* and *Escherichia coli* to antibiotics by the sesquiterpenoids nerolidol, farnesol, bisabolol, and apritone", *Antimicrobial Agents and Chemotherapy*; 47(10):3357-3360 (2003).
de Abreu Gonzaga et al., "Composition and antibacterial activity of the essential oils from Zanthoxylum rhoifolium", *Planta Med.* 69(8)773-775 (2003).

Garcia, et al.; "Virucidal activity of essential oils from aromatic plants of San Luis, Argentina", *Phytother. Res.*, 17(9):1073-1075 (2003).
Gershon, et al., "Antifungal Properties of n-Alkanols, α, w-n-Alkanedoils, and w-Chloro-α-alkanols", *J. Pharm. Sci.*, 64(4):381-384 (2006).
Goren, et al., "Analysis of essential oil of *Coridothymus capitatus* (L.) and its antibacterial and antifungal activity", Z. Naturforsch., 58(9-10):(9-10):687-690 (2003).
Hajhashemi, et al., "Anti-inflammatory and analgesic properties of the leaf extracts and essential oil of Lavandula angustifolia Mill", *J. Ethnopharmacol.* 89(1):67-71 (2003).
Kupferwasser, et al., "Acetylsalicylic Acid Reduces Vegetation Bacterial Density, Hematogenous Bacterial Dissemination, and Frequency of Embolic Events in Experimental *Staphylococcus aureus* Endocarditis Through Antiplatelet and Antibacterial Effects", *Circulation*, vol. 99:2791-2797 (1999).
Kupferwasser, et al., "Salicyclic Acid Attenuates Virulence in Endovascular Infections by Targeting Global Regulatory Pathways in *Staphylococcus aureus*," *Clin. Invest.*, 112(2):222-233 (2003).
Minami et al., "The inhibitory effect of essential oils on herpes simplex virus type-1 replication in vitro", *Microbial Immunol.* 47(a):681-684 (2003).
Paranagama et al., "Fungicidal and anti-aflatoxigenic effects of the essential oil of *Cymbopogon citratus* (DC.) Stapf. (lemongrass) against Aspergillis flavus Link. isolated from stored rice", *Lett. Appl. Microbiol.*; 37(1):86-90 (2003).
Schuhmacher, et al., "Virucidal effect of peppermint oil on the enveloped viruses herpes simplex virus type 1 and type 2 in vitro", *Phytomedicine.*, 10:504-510 (2003).
Shin, "Anti-Aspergillus activities of plant essential oils and their combination effects with ketoconazole or amphotericin B", *Arch. Pharm. Res.*, 26(5):389-393 (2003).
Silva et al.,"Analgesic and anti-inflammatory effects of essential oils of Eucalyptus", *J. Ethnopharmacol.*, 89(2-3);277-283 (2003).
Valero, et al., "Antibacterial activity of 11 essential oils against in Bacillus cereus in tyndallized carrot broth", *Int. J. Food Microbiol.*, 85(1-2):73-81 (2003).
Velluti et al., "Inhibitory effect of cinnamon, clove, lemongrass, oregano and palmarose essential oils on growth and fumonisin B1 production by Fusarium proliferatum in maize grain." *Int. J. Food Microbiol.*, 89:145-154 (2003).
Ayliffe, et al., "Hand disinfection: A comparison of various agents in laboratory and ward studies", *Journal of Hospital Infection*, 11(3):226-243 (1988).
Bettini Mercia de Fatima M., "Purification of Orange Peel Oil and Oil Phase by Vacuum Distillation", *Functional Food Ingredients and Nutraceuticals, Processing Technologies, Edited by john Shi, CPC Press* 2006, pp. 157-172.
Cancio, et al., "Burn wound infections" In: *Surgical Treatment: Evidence-Based and Problem-Oriented*, 2001.
Fang, et al., "Prospective clinical study of Hydron, a synthetic dressing, in delivery of an antimicrobial drug to second-degree burns", *J. Burn Care Rehabil.*, 8(3);206-209 (1987).
Fox, et al., "Comparative evalucation of zinc sulfadiazine and silver sulfadiazine in burn wound infection", *J. Burn Care Rehabil.*, 11(2):112-117 (1990).
Gaonkar, et al., "In vivo efficacy of an alcohol-based surgical hand disinfectant containing a synergistic combination of ethylhexylglycerin and preservatives", *Journal of Hospital Infection*, 63(4):412-417 (2006).
Gaonkar, et al., "An alcohol hand rub containing a synergistic combination of an emollient and preservatives: prolonged activity against transient pathogens", *Journal of Hospital Infection*, 59(1):12-18 (2005).
European Supplementary Search Report for EP 08780771.5, dated Dec. 17, 2012.
International Search Report and Written Opinion for PCT/US2012/052793, dated Nov. 19, 2012.
International Search Report and Written Opinion for PCT/US2012/063013, dated Jan. 4, 2013.
International Search Report and Written Opinion for PCT/US2012/037135, dated Oct. 16, 2012.

(56) References Cited

OTHER PUBLICATIONS

Choudhary, et al., "Solvent-free selective oxidation of benzyl alcohol and benzaldehyde by tert-butyl hydroperoxide using $MnO_4$-exchanged Mg-Al-hydrotalcite catalsysts", *Catalysis Letters*, 86(4):229-233 (2003).

Zhang, et al., "Antifungal Activities of Major Tea Leaf Volatile Constituents toward Colletorichum Camelliae Massea", *Journal of Agricultural and Food Chemistry*, 54(11):3936-3940 (2006).

Nazer, et al., "Combinations of food antimicrobials at low levels to inhibit the growth of *Salmonella* sv. Typhimurium: a synergistic effect?", *Food Microbiology*, 22:391-398 (2005).

"Sheer Moisturizer Hand Sanitizer", *Mintel Global New Products Database*, pp. 1-4 (2010) Retrieved from Internet: URL:www.gnpd.com [Retrieved on Aug. 34, 2013].

"Antibacterial Wet Wipes", *Mintel Global New Products Database*, pp. 1-2 (2008) Retrieved from the Internet: URL:www.gnpd.com [Retrieved on Sep. 24, 2013].

Cowan, "Plant product as antimicrobial agents"*Clinical Microbiology Reviews*, 12(4):564-582 (1999).

Nannapanerni et al., "Antimicrobial activity of commercial citrus-based natural extracts against *Escherichia coli* O157:H7 isolates and mutant strains", *Foodborne Pathog Dis.*, 5(5):695-699 (2008).

International Search Report and Written Opinion for PCT/US2013/071731, dated Feb. 12, 2014.

Keeven et al., "Evaluating the perservative effectiveness of RGP lens care solutions", *The Contact Lens Association of Opththalmologists Journal*, 21(4):238-241 (1995).

El-Zemity et al., "Antifungal activity of some essential oils and their major chemical constituents agains some phytopathogenic fungi", *Journal of Pest Control and Environmental Science*, 12(1):87-99 (2005).

U.S. Appl. No. 12/694,119, Nov. 5, 2015 Amendment and Request for Continued.

\* cited by examiner

BROAD SPECTRUM NATURAL PRESERVATIVE COMPOSITION

CROSS-REFERENCE TO RELATED APPLICATION

This application is a continuation in part of International Application Serial No. PCT/US12/068107, filed Dec. 6, 2012, and which published as WO/2013/086094 on Jun. 13, 2013, which claims the benefit of and priority to U.S. Provisional Application Ser. No. 61/567,372, filed Dec. 6, 2011, all of which are hereby incorporated by reference in their entireties, and to each of which priority is claimed.

1. INTRODUCTION

Disclosed are combinations of alcohol, such as benzyl alcohol, ethyl alcohol or phenyl ethanol, and cinnamon bark oil, cinnamaldehyde, galangal oil, thyme oil, thymol, botanical extracts or combinations thereof, for use in personal care formulations.

2. BACKGROUND

In the past, synthetic preservatives such as parabens, imidiazolidinyl urea, DMDM hydantoin, triclosan and quaternary ammonium compounds have been the mainstay of preservatives in cosmetics, toiletries, health and personnel care products. Recently the popularity of traditional preservatives has greatly diminished around the world due to regulatory, environmental and health issues. Concerns over traditional preservatives have resulted in the search for natural alternatives. There has been a significant increase in the use of plant products in many areas of human health such as treating common diseases and as preservatives in personal care products.

The ideal preservative should have broad spectrum antimicrobial activity and the ability to be used in various types of formulations without affecting the function, color or odor of the final product. A preservative composition desirably inactivates bacteria, fungi as well as yeast in both cationic and anionic formulations. Additionally, preservatives should have a low risk of irritation and sensitizing potential. While certain essential oils have antibacterial activity and may be suitable in that regard, most have a distinct odor and are therefore not universally appropriate for use as preservatives in personal care products.

3. SUMMARY

Disclosed herein are preservative compositions comprising effective amounts of an alcohol, for example, benzyl alcohol ("BA"), ethyl alcohol or phenyl ethanol ("PE"), and cinnamon bark oil ("CB" or "CBO"), cinnamaldehyde ("CMA"), or galangal oil, each of which are preferably obtained from natural sources. These preservatives have been observed to show broad spectrum anti microbial efficacy in both anionic and cationic formulations. In certain non-limiting embodiments, such compositions further comprise tetrahydrocurcuminoid ("THC"), phenyl ethanol and/or orange oil ("OR") or rosemary oil ("RM").

In certain embodiments, the compositions of the present application comprise BA (for example, between about 0.1 and 0.8% weight/weight ("w/w")), PE (for example, between about 0 and 0.5% w/w), THC and/or curcumin (for example, between about 0.03 and 0.2% w/w), CB (for example, between about 0.01 and 0.3% w/w), benzoic acid (for example, between about 0.1 and 0.3% w/w). In certain embodiments, the compositions further comprise thymol (for example, between about 0.05 and 0.1% w/w), and one or more botanical extract selected from the group consisting of grapefruit seed extract, calendula extract, and combinations thereof (for example, between about 0.5 and 1% w/w). In certain embodiments, the compositions can be used in personal care products, and topical antimicrobial and/or antifungal compositions such as creams, wherein such compositions can be for human or veterinary use. In certain embodiments, the compositions can be used in a disinfectant or pesticide.

4. DETAILED DESCRIPTION

For clarity but not by way of limitation, the detailed description is divided into the following subsections,
  (i) active agents;
  (ii) topical disinfectants;
  (iii) personal care formulations;
  (iv) pesticides;
  (v) disinfectants for food
  (vi) additional ingredients; and
  (vii) methods of use.

4.1 Active Agents

Disclosed herein are compositions comprising effective antimicrobial amounts of a combination of an alcohol, for example, benzyl alcohol ("BA"), ethyl alcohol or phenyl ethanol, and one or more component selected from the group consisting of cinnamon bark oil ("CB" or "CBO"), cinnamaldehyde ("CMA"), thyme oil ("TO"), thymol ("TH"), galangal oil ("GG"), and botanical extracts selected from the group consisting of portulaca extract, wasabi extract, calendula extract or combinations thereof.

"Preservative effect" as used herein mean "antimicrobial effect." Antimicrobial effect is static or reduced growth of microbes such as one or more of bacteria (Gram positive and/or Gram negative), protozoa, yeast or fungi. Exemplary microbes which may be inhibited include *Staphylococcus aureus, Staphylococcus epidermidis, Enterococcus, Escherichia coli, Pseudomonas aeruginosa, Candida albicans*, and *Aspergillus niger*.

Also disclosed are stock solutions that may be diluted in a personal care formulation to impart a preservative effect.

In certain non-limiting embodiments, the amount of BA in a composition is between about 0.1 and 1.0 percent w/w, or between about 0.1 and 0.8 percent w/w, or between about 0.3 and 0.8 percent w/w, or between about 0.4 and 0.8 percent w/w, or about 0.5 percent w/w. In certain non-limiting embodiments, the amount of BA in a stock solution is between about 30 and 80 percent w/w. "About" as used herein means plus or minus 10 percent of the recited value. In certain non-limiting embodiments, the BA is obtained from a natural source. In other non-limiting embodiments the BA is synthetic.

In certain non-limiting embodiments, the compositions of the present application may comprise alcohol, for example, but not limited to, ethyl alcohol. In certain non-limiting embodiments, the amount of alcohol is between about 0.1 and 5 percent w/w, or between about 0.1 and 2.0 percent w/w, or between about 0.1 and 1.0 percent w/w, or between about 0.1 and 0.8 percent w/w, or between about 0.3 and 0.8 percent w/w, or between about 0.4 and 0.8 percent w/w, or about 0.5 percent w/w. In certain non-limiting embodiments, the amount of alcohol in a stock solution is between about 30 and 80 percent w/w. In certain non-limiting embodiments, the alcohol is obtained from a natural source. In other non-limiting embodiments the alcohol is synthetic.

In certain non-limiting embodiments, the compositions of the present application may comprise phenyl ethanol. In certain non-limiting embodiments, the amount of phenyl ethanol is between about 0.05 and 2.0 percent w/w, or between about 0.05 and 1.0 percent w/w, or between about 0.1 and 2.0 percent w/w, or between about 0.1 and 0.5 percent w/w. In certain non-limiting embodiments, the amount of phenyl ethanol in a stock solution is between about 10 and 40 percent w/w. In certain non-limiting embodiments, the phenyl ethanol is obtained from a natural source. In other non-limiting embodiments the phenyl ethanol is synthetic.

In certain non-limiting embodiments, the amount of CB, CMA, thymol or GG is between about 0.01 and 0.5 percent w/w, or between about 0.01 and 0.2 percent w/w, or between about 0.05 and 0.5 percent w/w or between about 0.05 and 0.2 percent w/w. In certain non-limiting embodiments, the amount of CB, CMA or GG in a stock solution is between about 5 and 20 percent w/w.

Such compositions may further comprise THC to further enhance the antimicrobial activity provided by an alcohol, for example, BA, ethyl alcohol or phenyl ethanol, and CB, CMA or GG. In certain non-limiting embodiments, the amount of THC is between about 0.01 and 0.2 percent w/w or between about 0.025 and 0.05 percent w/w, or between about 0.03 and 0.1 percent w/w. In certain non-limiting embodiments, the amount of THC in a stock solution is between about 2 and 15 percent w/w.

In certain non-limiting embodiments, the compositions of the present application may, whether THC is also present or not, further comprise phenyl ethanol. In certain non-limiting embodiments, the amount of phenyl ethanol is between about 0.05 and 2.0 percent w/w, or between about 0.05 and 1.0 percent w/w, or between about 0.1 and 2.0 percent w/w, or between about 0.1 and 0.5 percent w/w. In certain non-limiting embodiments, the amount of phenyl ethanol in a stock solution is between about 10 and 40 percent w/w.

Any of the foregoing compositions may further comprise glycerin, a natural gelling agent, for example, but not limited to xanthan gum, aloe gel, sangelose, hydroxyl methyl cellulose, hydroxyl methyl cellulose derivatives, and combinations thereof, in an amount between about 10 and 40 percent w/w in a stock solution.

In particular, non-limiting embodiments, the composition comprises BA in an amount between 0.1 and 1 percent or between about 0.4 and 0.8 percent w/w, THC in an amount between about 0.05 and 1.0 percent or between about 0.1 and 0.5 percent w/w, and CB in an amount between about 0.05 and 0.5 percent or between about 0.05 and 0.2 percent w/w, and optionally phenyl ethanol, where present, in an amount between about 0.05 and 1 percent or between about 0.1 and 0.5 percent w/w. In a related non-limiting embodiment, a stock solution comprises BA in an amount between about 30 and 80 percent w/w, THC in an amount between 2 and 15 percent w/w and CB in an amount between about 5 and 20 percent, and optionally phenyl ethanol in an amount between 10 and 40 percent.

In one specific non-limiting embodiment, the composition comprises BA at about 0.5 percent w/w, THC at about 0.05 percent w/w, and CB at about 0.1 percent w/w, and optionally phenyl ethanol at about 0.25 percent w/w.

Any of the compositions of the present application may further comprise an agent that masks the odor of CB or otherwise enhances the olfactory appeal of the composition. In certain embodiment the making agent is an essential oil. In certain embodiments, the compositions of the present application comprise an essential oil, for example but not limited to, orange oil ("OR"), citral ("CL"), rosemary oil ("RM") cedar wood oil ("CW"), sandal wood oil ("SW"), sandal wood oil related fragrances, ylang ylang oil ("YL"), patchouli oil ("PO"), vetiver oil ("VO"), lemongrass oil ("LG"), thyme oil ("TO") and/or thymol ("TH"), for example, in an amount between about 0.02 and 1 percent w/w or between about 0.1 and 0.5 percent w/w. In certain non-limiting embodiments, the amount of essential oil such as OR, RM, CL, CW, SW, PO, VO, LG, TO, TH and/or YL in a stock solution is between about 2 and 30 percent w/w.

In particular, non-limiting embodiments, the composition comprises BA in an amount between 0.1 and 1 percent or between about 0.4 and 0.8 percent w/w, THC in an amount between about 0.05 and 1.0 percent or between about 0.1 and 0.5 percent w/w, CB in an amount between about 0.05 and 0.5 percent or between about 0.05 and 0.2 percent w/w, phenyl ethanol in an amount between about 0.05 and 1 percent or between about 0.1 and 0.5 percent w/w, and an essential oil selected from OR, RM, CL, CW, SW, PO, VO, LG, TH or YL in an amount between about 0.05 and 1 percent, or between about 0.05 and 0.1 percent, or between about 0.05 and 0.5 percent, or between about 0.1 and 0.5 percent, or between about 0.1 and 0.3 percent w/w. In a related non-limiting embodiment, a stock solution comprises BA in an amount between about 30 and 80 percent w/w, THC in an amount between 2 and 15 percent w/w, CB in an amount between about 5 and 20 percent, phenyl ethanol in an amount between 10 and 40 percent, and OR, RM, CL, CW, SW, and/or YL in an amount between 5 and 30 percent w/w.

In one specific non-limiting embodiment, the composition comprises BA at about 0.5 percent w/w, THC at about 0.05 percent w/w, CB at about 0.1 percent w/w, phenyl ethanol at about 0.25 percent w/w, and OR or RM at about 0.2 percent w/w.

In certain non-limiting embodiments, the composition, whether it comprises THC and/or phenyl ethanol or not, further comprises thymol ("TH"). In certain non-limiting embodiments, the amount of TH is between about 0.05 and 0.5 percent w/w or between about 0.05 and 0.2 percent w/w. In certain non-limiting embodiments, the amount of TH in a stock solution is between about 5 and 20 percent w/w.

In particular, non-limiting embodiments, the composition comprises BA in an amount between 0.1 and 1 percent or between about 0.4 and 0.8 percent w/w, GG in an amount between about 0.05 and 0.5 percent or between about 0.05 and 0.2 percent w/w, phenyl ethanol in an amount between about 0.05 and 1 percent or between about 0.1 and 0.5 percent w/w, TH in an amount between about 0.05 and 0.5 percent or between about 0.05 and 0.2 percent w/w, and an essential oil selected from OR, RM, CL, CW, SW, and/or YL in an amount between about 0.05 and 1 percent or between about 0.1 and 0.5 percent w/w. In a related non-limiting embodiment, a stock solution comprises BA in an amount between about 30 and 80 percent w/w, GG in an amount between about 5 and 20 percent, phenyl ethanol in an amount between 10 and 40 percent, TH in an amount between about 5 and 20 percent, and OR, RM, CL, CW, SW, and/or YL in an amount between 5 and 30 percent w/w.

In one specific non-limiting embodiment, the composition comprises BA at about 0.5 percent w/w, GG at about 0.1 percent w/w, phenyl ethanol at about 0.2 percent w/w, TH at about 0.1 percent w/w and OR or RM at about 0.2 percent w/w.

In one specific non-limiting embodiment, the composition comprises BA at about 0.5 percent w/w, THC at about 0.05 percent w/w, CB at about 0.1 percent w/w, phenyl ethanol at about 0.25 percent w/w, and OR or RM at about 0.2 percent w/w.

In one specific non-limiting embodiment, the composition comprises BA at about 0.5 percent w/w, GG at about 0.1 percent w/w, phenyl ethanol at about 0.2 percent w/w, TH at about 0.1 percent w/w and CL at about 0.1 percent w/w.

In certain non-limiting embodiments the compositions described above may further comprise propanediol, for example synthetic propanediol or Zemea®. In other non-limiting embodiments the compositions described herein do not contain propanediol. In certain non-limiting embodiments the compositions described herein do not contain any alkanediol.

In certain non-limiting embodiments, all of the active components as described above are obtained from natural sources rather than synthetically produced.

In certain non-limiting embodiments, the composition does not comprise a paraben compound.

In certain non-limiting embodiments, the composition does not further comprise antimicrobial effective amounts of one or more of the following antimicrobial agents: quaternary ammonium compounds, biguanides, chlorinated phenols, triclosan, chlorhexidine or chlorhexidine salt, phenoxyethanol, povidone iodine, or para chlorometa xylenol. In certain non-limiting embodiments, the composition does not further comprise antimicrobial effective amounts of any of the following antimicrobial agents: quaternary ammonium compounds, biguanides, chlorinated phenols, triclosan, chlorhexidine or chlorhexidine salt, phenoxyethanol, povidone iodine, aliphatic alcohol, or para chlorometa xylenol.

In certain non-limiting embodiments, the composition does not contain any fruit acid.

In certain non-limiting embodiments, the compositions of the present application further comprise a botanical extract, for example, but not limited to, a botanical extract selected from the group consisting of portulaca extract, wasabi extract, calendula extract and combinations thereof. In certain non-limiting embodiments, the amount of botanical extract is between about 0.02 and 2.0 percent w/w, or between about 0.02 and 1.0 percent w/w, or between about 0.05 and 1.0 percent w/w, or between about 0.1 and 2.0 percent w/w, or between about 0.1 and 0.5 percent w/w. In certain non-limiting embodiments, the amount of botanical extract is between about 0.02 and 0.2 percent w/w. In certain non-limiting embodiments, the amount of botanical extract in a stock solution is between about 10 and 40 percent w/w.

In certain embodiments, the compositions of the present application comprise BA (for example, between about 0.01 and 2% w/w, or between about 0.05 and 1% w/w, or between about 0.1 and 0.8% w/w, or between about 0.2 and 0.6% w/w), PE (for example, between about 0 and 2% w/w, or between about 0.01 and 0.8% w/w, or between about 0.1 and 0.6% w/w, or between about 0.2 and 0.5% w/w, or between about 0 and 0.5% w/w), THC and/or curcumin (for example, between about 0.01 and 1% w/w, or between about 0.1 and 0.5% w/w, or between about 0.2 and 0.4% w/w, or between about 0.03 and 0.2% w/w), CB (for example, between about 0.001 and 1% w/w, or between about 0.01 and 0.8% w/w, or between about 0.1 and 0.6% w/w, or between about 0.2 and 0.4% w/w, or between about 0.01 and 0.3% w/w), benzoic acid (for example, between about 0.01 and 1% w/w, or between about 0.1 and 0.8% w/w, or between about 0.2 and 0.6% w/w, or between about 0.1 and 0.3% w/w). In certain embodiments, the compositions further comprise thymol (for example, between about 0.001 and 1% w/w, or between about 0.01 and 0.8% w/w, or between about 0.1 an 0.6% w/w, or between about 0.2 and 0.4% w/w, or between about 0.05 and 0.1% w/w), and one or more botanical extract selected from the group consisting of grapefruit seed extract, calendula extract, and combinations thereof (for example, between about 0.01 and 2% w/w, or between about 0.1 and 1.5% w/w, or between about 0.2 and 1% w/w, or between about 0.5 and 1% w/w, or between about 0.6 and 0.8% w/w).

In certain non-limiting embodiments, the compositions of the present application are formulated in a base. In certain non-limiting embodiments, the base is a cationic emulsion. In certain non-limiting embodiments, the base is an anionic emulsion. In certain non-limiting embodiments, the base comprises one or more of water, Ucare Jr 30 M, Incroquat TMS, Polawax NF, petrolatum, stearyl alcohol, polyoxyl 40 stearate, propylene glycol, isopropyl myristate, sorbitan oleate, mineral oil, ceteareth 25, cetearyl alcohol, glyceryl stearate, and monoglyceryl citrate.

In one specific non-limiting embodiment, the base comprises the following components:

| Ingredient | % w/w |
| --- | --- |
| Water | 75.5 |
| UcareJr 30 M | 0.24 |
| Incroquat TMS | 2.4 |
| Polawax NF | 2.4 |
| Petrolatum | 4.8 |
| Stearyl alcohol | 6.6 |
| Polyoxyl 40 stearate | 1.6 |
| Propylene glycol | 1.6 |
| Isopropyl myristate | 3.2 |
| Sorbitan oleate | 1.6 | pH 6.5

In one specific non-limiting embodiment, the base comprises the following components:

| Ingredient | % w/w |
| --- | --- |
| Water | 78.0 |
| Propylene glycol | 2.0 |
| Mineral oil | 9.5 |
| Ceteareth 25 | 2.5 |
| Cetearyl Alcohol | 4.0 |
| Glyceryl stearate | 2.0 |
| Monoglyceryl citrate | 2.0 | pH 5.0

In one set of non-limiting embodiments, the composition comprises the following components:

| Ingredients | % weight/weight (w/w) |
| --- | --- |
| Benzyl alcohol | 0.3-0.8 |
| Tetrahydrocurcumanoid | 0.025-0.05 |
| Cinnamon bark oil | 0.05-0.1 |
| Lemon grass oil | 0.05-0.1 |
| Cedar wood oil | 0.1-0.3 |
| Phenyl ethanol | 0-0.5 |

In certain embodiments, the composition further comprises an odor masking agent. In certain embodiments, the odor masking agent is selected from the group consisting of patchouli oil, vetiver oil, sandal wood oil and sandal wood oil related fragrances.

In one specific non-limiting embodiment, the composition comprises the following components:

| Ingredients | % w/w |
| --- | --- |
| Benzyl alcohol | 0.5 |
| Tetrahydrocurcumanoid | 0.05 |
| Cinnamon bark oil | 0.10 |
| Lemon grass oil | 0.075 |
| Cedar wood oil | 0.2 |
| Phenyl ethanol | 0.3 |

In certain embodiments, the composition further comprises an odor masking agent. In certain embodiments, the odor masking agent is selected from the group consisting of patchouli oil, vetiver oil, sandal wood oil and sandal wood oil related fragrances.

In one set of non-limiting embodiments, the composition comprises the following components:

| Ingredients | % w/w |
| --- | --- |
| Benzyl alcohol | 0.3-0.8 |
| Tetrahydrocurcumanoid | 0.025-0.05 |
| Cinnamon bark oil | 0.05-0.1 |
| Lemon grass oil | 0.05-0.1 |
| Cedar wood oil | 0.1-0.3 |

In certain embodiments, the composition further comprises an odor masking agent. In certain embodiments, the odor masking agent is selected from the group consisting of patchouli oil, vetiver oil, sandal wood oil and sandal wood oil related fragrances.

In one specific non-limiting embodiment, the composition comprises the following components:

| Ingredients | % w/w |
| --- | --- |
| Benzyl alcohol | 0.5 |
| Tetrahydrocurcumanoid | 0.05 |
| Cinnamon bark oil | 0.10 |
| Lemon grass oil | 0.075 |
| Cedar wood oil | 0.1 |

In certain embodiments, the composition further comprises an odor masking agent. In certain embodiments, the odor masking agent is selected from the group consisting of patchouli oil, vetiver oil, sandal wood oil and sandal wood oil related fragrances.

In one set of non-limiting embodiments, the composition comprises the following components:

| Ingredients | % w/w |
| --- | --- |
| Benzyl alcohol | 0.3-0.8 |
| Tetrahydrocurcumanoid | 0.025-0.05 |
| Cinnamon bark oil | 0.05-0.1 |
| Lemon grass oil | 0.05-0.1 |
| Thymol | 0.05-0.5 |
| Cedar wood oil | 0.05-0.3 |

In certain embodiments, the composition further comprises an odor masking agent. In certain embodiments, the odor masking agent is selected from the group consisting of patchouli oil, vetiver oil, sandal wood oil and sandal wood oil related fragrances.

In one specific non-limiting embodiment, the composition comprises the following components:

| Ingredients | % w/w |
| --- | --- |
| Benzyl alcohol | 0.5 |
| Tetrahydrocurcumanoid | 0.05 |
| Cinnamon bark oil | 0.05 |
| Lemon grass oil | 0.05 |
| Thymol | 0.05 |
| Cedar wood oil | 0.1 |

In certain embodiments, the composition further comprises an odor masking agent. In certain embodiments, the odor masking agent is selected from the group consisting of patchouli oil, vetiver oil, sandal wood oil and sandal wood oil related fragrances.

In one specific non-limiting embodiment, the composition comprises the following components:

| Ingredients | % w/w |
| --- | --- |
| Benzyl alcohol | 0.1 |
| Tetrahydrocurcumanoid | 0.05 |
| Cinnamon bark oil | 0.05 |
| Lemon grass oil | 0.05 |
| Cedar wood oil | 0.05 |

In certain embodiments, the composition further comprises an odor masking agent. In certain embodiments, the odor masking agent is selected from the group consisting of patchouli oil, vetiver oil, sandal wood oil and sandal wood oil related fragrances.

In certain embodiment, the compositions of the present application do not comprise benzyl alcohol.

In one set of non-limiting embodiments, the composition comprises the following components:

| Ingredients | % w/w |
| --- | --- |
| Cinnamon bark oil | 0.01-0.2 |
| Tetrahydrocurcumanoid | 0.025-0.05 |
| Alcohol | 0.1-2.0 |

In one specific non-limiting embodiment, the composition comprises the following components:

| Ingredients | % w/w |
| --- | --- |
| Cinnamon bark oil | 0.1 |
| Tetrahydrocurcumanoid | 0.05 |
| Alcohol | 0.5 |

In one set of non-limiting embodiments, the composition comprises the following components:

| Ingredients | % w/w |
| --- | --- |
| Cinnamon bark oil | 0.01-0.2 |
| Tetrahydrocurcumanoid | 0.025-0.05 |
| Phenyl ethanol | 0.1-2.0 |

In one specific non-limiting embodiment, the composition comprises the following components:

| Ingredients | % w/w |
| --- | --- |
| Cinnamon bark oil | 0.1 |
| Tetrahydrocurcumanoid | 0.05 |
| Phenyl ethanol | 0.5 |

In one set of non-limiting embodiments, the composition comprises the following components:

| Ingredients | % w/w |
| --- | --- |
| Cinnamon bark oil | 0.01-0.2 |
| Tetrahydrocurcumanoid | 0.025-0.05 |
| Alcohol | 0.1-2.0 |
| Thymol | 0.02-0.2 |

In one specific non-limiting embodiment, the composition comprises the following components:

| Ingredients | % w/w |
| --- | --- |
| Cinnamon bark oil | 0.1 |
| Tetrahydrocurcumanoid | 0.05 |
| Alcohol | 0.5 |
| Thymol | 0.05 |

In one set of non-limiting embodiments, the composition comprises the following components:

| Ingredients | % w/w |
| --- | --- |
| Cinnamon bark oil | 0.01-0.2 |
| Tetrahydrocurcumanoid | 0.025-0.05 |
| Alcohol | 0.1-2.0 |
| *Portulaca* extract | 0.02-0.2 |

In one specific non-limiting embodiment, the composition comprises the following components:

| Ingredients | % w/w |
| --- | --- |
| Cinnamon bark oil | 0.1 |
| Tetrahydrocurcumanoid | 0.05 |
| Alcohol | 0.5 |
| *Portulaca* extract | 0.05 |

In one specific non-limiting embodiment, the composition comprises the following components:

| Ingredients | % w/w |
| --- | --- |
| Benzyl alcohol | 0.5 |
| Cinnamon bark oil | 0.05 |
| Thymol | 0.05 |
| Tetrahydrocurcumanoid | 0.05 |

In one specific non-limiting embodiment, the composition comprises the following components:

| Ingredients | % w/w |
| --- | --- |
| Benzyl alcohol | 0.5 |
| Cinnamon bark oil | 0.10 |
| Thymol | 0.05 |
| Tetrahydrocurcumanoid | 0.05 |

In one set of non-limiting embodiments, the composition comprises the following components:

| Ingredients | % w/w |
| --- | --- |
| Benzyl alcohol | 0.1-1.0 |
| Thymol | 0.03-0.1 |
| *Portulaca* extract | 0.2-2.0 |
| Ethanol | 0.05-1.0 |

In one set of non-limiting embodiments, the composition comprises the following components:

| Ingredients | % w/w |
| --- | --- |
| Benzyl alcohol | 0.5 |
| Thymol | 0.05 |
| *Portulaca* extract | 0.5 |
| Ethanol | 0.2 |

In one set of non-limiting embodiments, the composition comprises the following components:
Preservative Composition 1:

| Ingredients | % w/w Stock | % w/w Use level in products |
| --- | --- | --- |
| BA (Benzyl alcohol) | 30-50 | 0.3-0.5 |
| THC (Tetrahydrocurcuminiod) | 5-10 | 0.05-0.1 |
| Benzoic acid | 10-20 | 0.1-0.2 |
| CBO (Cinnamon Bark oil) | 3-5 | 0.03-0.05 |

In one set of non-limiting embodiments, the composition comprises the following components:
Preservative Composition 2:

| Ingredients | % w/w Stock | % w/w Use level in products |
| --- | --- | --- |
| BA | 30-50 | 0.3-0.5 |
| THC | 5-10 | 0.05-0.1 |
| Benzoic acid | 10-20 | 0.1-0.2 |
| CBO (Cinnamon Bark oil) | 1-5.0 | 0.01-0.05 |
| Thymol | 3-5 | 0.03-0.05 |

4.2 Topical Disinfectants

Disclosed herein are compositions that may be comprised in disinfectant compositions that may be used topically to reduce the number and/or growth of microbes, for example, bacteria and/or fungus, on the skin of a human or non-human animal. The disinfectant may be a wash solution, a lotion, a cream, or a splash and/or may be comprised in a wipe.

In certain embodiments, the disinfectant composition comprises the recited active agents and a suitable solvent. Non-limiting examples of suitable solvents 10 include water, ethanol, glycerin, octoxyglycerin, and mixtures thereof.

Disclosed herein is a method of reducing the number and/or growth of microbes on the skin of a subject (for example, a human subject) comprising applying to the skin a topical disinfectant composition as set forth herein. Microbes, the numbers and/or growth of which are reduced, include but are not limited to one or more of *Staphylococcus aureus* (including methicillin resistant *Staphylococcus aureus*), *Staphylococcus epidermidis*, *Escherichia coli*, *Pseudomonas aeruginosa*, *Candida albicans*, *Aspergillus niger* and *Listeria monocytogenes*.

In one set of non-limiting embodiments, the composition comprises the following components:

| Antimicrobial topical composition Formulation A | |
|---|---|
| Ingredients | % w/w |
| Actives | |
| BA | 1.0 |
| CBO | 0.1 |
| THC | 0.1 |
| Benzoic acid | 0.2 |
| Thymol | 0.1 |
| *Calendula* extract | 1.0 |
| Inactives | |
| Water | 75 |
| Grapefruit seed extract | 0.5 |
| Polyquaternium 10 | 0.30 |
| Incroquat TMS | 2.4 |
| Polawax NF | 2.4 |
| Petrolatum | 4.8 |
| Steatyl alcohol | 6.6 |
| Polyoxyl 40 stearate | 1.6 |
| Propylene glycol | 1.6 |
| Isopropyl myristate | 3.2 |
| Sorbitan oleate | 1.6 |

In one set of non-limiting embodiments, the composition comprises the following components:

| Antifungal topical composition Formulation B | |
|---|---|
| Ingredients | % w/w |
| Actives | |
| BA | 1.0 |
| CBO | 0.3 |
| THC | 0.1 |
| Benzoic acid | 0.2 |
| Thymol | 0.1 |
| *Calendula* extract | 1.0 |
| Inactives | |
| Water | 74.8 |
| Grapefruit seed extract | 0.5 |
| Polyquaternium 10 | 0.30 |
| Incroquat TMS | 2.4 |
| Polawax NF | 2.4 |
| Petrolatum | 4.8 |
| Stearyl alcohol | 6.6 |
| Polyoxyl 40 stearate | 1.6 |
| Propylene glycol | 1.6 |
| Isopropyl myristate | 3.2 |
| Sorbitan oleate | 1.6 |

In certain embodiments, Formulation B can be used as an antifungal cream, for example, for use in treating Athlete's foot (for example, skin infection caused by *Epidermophyton floccosum* or fungi of the *Trichophyton* genus such as *T. rubrum* or *T. mentagrophytes*). In certain embodiments, Formulation B can be comprised in a composition with or without additional antifungal agents. In certain embodiments, Formulation A and/or B can be also used in a topical composition, such as a cream, for veterinary use as described herein.

4.3 Personal Care Formulations

In non-limiting embodiments, the compositions disclosed herein are embodied as gels, tonics, lotions or creams such as but not limited to hand cream, liquid or cream makeup, and other cosmetic products, hair conditioners or other hair care products such as setting gels or tonics, shampoos, soaps, wipe formulations or diaper rash ointments or creams. The formulations may be applied to humans or non-human animals (for example, for veterinary or agricultural purposes).

In a subset of non-limiting embodiments, the present subject matter provides for veterinary products for care of any domestic animal, including but not limited to cats, dogs, birds, rodents, rabbits, horses, cows and cattle, sheep, goats, etc.

Non-limiting examples of veterinary care products which may utilize the compositions of the present subject matter include pet shampoo, pet cleansing wipes including body wipes, ear wipes, eye wipes, dental wipes, toothpaste, ear cleaning liquid, cage cleaner, surface cleaner for housebreaking accidents, topical creams, ointments, teat dip therapeutic for mastitis and liquid to be applied to pet's skin (as in a "body splash").

In one set of non-limiting embodiments, the composition comprises the following components:

| Diaper Rash cream Formulation C | |
|---|---|
| Ingredients | % w/w |
| Actives | |
| BA | 1.0 |
| CBO | 0.1 |
| THC | 0.1 |
| Thymol | 0.1 |
| Benzoic acid | 0.2 |
| *Calendula* extract | 1.0 |
| Inactives | |
| Water | 67.6 |
| Grapefruit seed extract | 0.5 |
| Polyquaternium 10 | 0.24 |
| Incroquat TMS | 1.4 |
| Polawax NF | 1.4 |
| Petrolatum | 4.8 |
| Stearyl alcohol | 6.6 |
| Polyoxyl 40 stearate | 1.6 |
| Propylene glycol | 1.6 |
| Isopropyl myristate | 3.2 |
| Sorbitan oleate | 1.6 |
| Silicone (Shin Etsu) KP 545 | 10.0 |

In certain embodiments, Formulation C can be used as an antifungal diaper rash composition, such as, for example, a cream. In certain embodiments, Formulation C can be used as an antifungal composition for use in treating geriatric patients. In certain embodiments, Formulation C can be comprised in a composition with or without additional antifungal agents.

4.4 Pesticides

In a subset of non-limiting embodiments, the present subject matter provides for pesticides comprising the formulations outlined above and described herein. In non-limiting embodiments, pesticides of the present subject matter include the following.

In one set of non-limiting embodiments, the composition comprises the following components:

| Pesticide Formulation Formulation D | |
|---|---|
| Ingredients | % w/w |
| Actives | |
| BA | 2.0 |
| CBO | 0.1 |
| Curcumin | 0.2 |
| Thymol | 0.1 |
| Cedarwood oil | 0.3 |
| Curry leaf oil | 0.2 |
| Benzoic acid | 0.2 |
| Lemongrass oil | 0.2 |
| Inactives | |
| Alcohol | 15.0 |
| Water | 76.7 |
| Natural Emulsifier | 5.0 |

4.5 Disinfectants for Food

In certain embodiments, the compositions disclosed herein are compositions that may be comprised in disinfectant compositions that may be used to reduce the number and/or growth of microbes on food products such as but not limited to vegetables, fruit, meat, poultry and fish. The disinfectant may be used by one or more of the original food producer or a food processor or the consumer. The food item may be washed, dipped, or soaked (for example, for between about 30 seconds and 1 hour or between about 30 seconds and 5 minutes) in the disinfectant composition, optionally followed by rinsing with water prior to consumption.

In certain embodiments the composition is a stock solution comprising the recited active agents and a suitable solvent. Non-limiting examples of suitable solvents include water, ethanol, glycerin, octoxyglycerin, and mixtures thereof.

As a non-limiting example, the stock disinfectant can be incorporated into the final product at a use level of between about 0.01 and 10 percent w/w.

Disclosed herein is a method of reducing the number and/or growth of microbes in or on a food product comprising exposing the food product to a disinfectant composition as set forth herein. Microbes (for example, bacteria and/or fungi), the numbers and/or growth of which are reduced, include but are not limited to one or more of *Aspergillus niger, Candida albicans, Staphylococcus aureus, Staphylococcus epidermidis, Escherichia coli, Pseudomonas aeruginosa, Enterococcus, Streptococcus* species, *Salmonella* species (e.g. *typhimurium, enteritidis*) and *Listeria monocytogenes*.

In one set of non-limiting embodiments, the composition comprises the following components:

| Food disinfectant formulation Formulation E | |
|---|---|
| Ingredients | % w/w |
| Actives | |
| BA | 1.0 |
| CBO | 0.1 |
| Curcumin | 0.2 |
| Thymol | 0.1 |
| Coriander leaf oil | 0.2 |
| Benzoic acid | 0.2 |
| Grapefruit seed extract | 0.5 |
| Inactives | |
| Natural glycerin | 5.0 |
| Water | 77.4 |
| Natural Emulsifier | 5.0 |

4.6 Additional Ingredients

The compositions may contain additional components known in the art for use in personal care compositions.

In certain non-limiting embodiments, the composition does not contain a petroleum-derived component.

In certain non-limiting embodiments, the composition may comprise a polyethylene oxide (Polyox) hydrogel polymer which, without being bound to any particular theory, can help the skin retain moisture.

In certain non-limiting embodiments, the composition may comprise an anti-irritant component, for example a zinc salt, such as zinc gluconate, alpha bisabolol, aloe gel/leaf juice, and combinations thereof. Further non-limiting examples of zinc salts that may be used include zinc acetate, zinc butyrate, zinc citrate, zinc glycerate, zinc glycolate, zinc formate, zinc lactate, zinc picolinate, zinc propionate, zinc salicylate, zinc tartrate, zinc undecylenate, and combinations thereof.

For example, a composition disclosed herein may further comprise a thickening and/or gelling agent such as stearyl alcohol, cationic hydroxy ethyl cellulose (Ucare; JR30), hydroxy propyl methyl cellulose, hydroxy propyl cellulose (Klucel), chitosan pyrrolidone carboxylate (Kytamer), behenyl alcohol, zinc stearate, emulsifying waxes, including but not limited to Incroquat and Polawax, an addition polymer of acrylic acid, a resin such as Carbopol® ETD 2020, guar gum, acacia, acrylates/steareth-20 methacrylate copolymer, agar, algin, alginic acid, ammonium acrylate co-polymers, ammonium alginate, ammonium chloride, ammonium sulfate, amylopectin, attapulgite, bentonite, C9-15 alcohols, calcium acetate, calcium alginate, calcium carrageenan, calcium chloride, caprylic alcohol, carbomer 910, carbomer 934, carbomer 934P, carbomer 940, carbomer 941, carboxymethyl hydroxyethyl cellulose, carboxymethyl hydroxypropyl guar, carrageenan, cellulose, cellulose gum, cetearyl alcohol, cetyl alcohol, corn starch, damar, dextrin, dibenzlidine sorbitol, ethylene dihydrogenated tallowamide, ethylene diolamide, ethylene distearamide, gelatin, guar gum, guar hydroxypropyltrimonium chloride, hectorite, hyaluronic acid, hydrated silica, hydroxybutyl methylcellulose, hydroxyethylcellulose, hydroxyethyl ethylcellulose, hydroxyethyl stearamide-MIPA, isocetyl alcohol, isostearyl alcohol, karaya gum, kelp, lauryl alcohol, locust bean gum, magnesium aluminium silicate, magnesium silicate, magnesium trisilicate, methoxy PEG-22/dodecyl glycol copolymer, methylcellulose, microcrystalline cellulose, montmorillonite, myristyl alcohol, oat flour, oleyl alcohol, palm kernel alcohol, pectin, PEG-2M, PEG-5M, polyacrylic acid, polyvinyl alcohol, potassium alginate, potassium aluminium polyacrylate, potassium carrageenan, potassium chloride, potassium sulfate, potato starch, propylene glycol alginate, sodium acrylate/vinyl alcohol copolymer, sodium carboxymethyl dextran, sodium carrageenan, sodium cellulose sulfate, sodium chloride, sodium polymethacylate, sodium silicoaluminate, sodium sulfate, stearalkonium bentotnite, stearalkonium hectorite, stearyl alcohol, tallow alcohol, TEA-hydrochloride, tragacanth gum, tridecyl alcohol, tromethamine magnesium aluminium silicate, wheat flour, wheat starch, xanthan gum, abietyl alcohol, acrylinoleic acid, aluminum behenate, aluminum caprylate, aluminum dilinoleate, aluminum salts, such as distearate, and aluminum isostearates, beeswax, behenamide, butadiene/acrylonitrile copolymer, C29-70 acid, calcium behenate, calcium stearate, candelilla wax, carnauba, ceresin, cholesterol, cholesterol hydroxystearate, coconut alcohol, copal, diglyceryl stearate malate, dihydroabietyl alcohol, dimethyl lauramine oleate, dodecanoic acid/cetearyl alcohol/glycol copolymer, erucamide, ethylcellulose, glyceryl triacetyl hydroxystearate, glyceryl tri-acetyl ricinolate, glycol dibehenate, glycol di-octanoate, glycol distearate, hexanediol distearate, hydrogenated C6-14 olefin polymers, hydrogenated castor oil, hydrogenated cottonseed oil, hydrogenated lard, hydrogenated menhaden oil, hydrogenated palm kernel glycerides, hydrogenated palm kernel oil, hydrogenated palm oil, hydrogenated polyisobutene, hydrogenated soybean oil, hydrogenated tallow amide, hydrogenated tallow glyceride, hydrogenated vegetable glyceride, hydrogenated vegetable oil, Japan wax, jojoba wax, lanolin alcohol, shea butter, lauramide, methyl dehydroabietate, methyl hydrogenated rosinate, methyl rosinate, methylstyrene/vinyltoluene copolymer, microcrystalline wax, montan acid wax, montan wax, myristyleicosanol, myristyloctadecanol, octadecene/maleic anhyrdine copolymer, octyldodecyl stearoyl stearate, oleamide, oleostearine, ouricury wax, oxidized polyethylene, ozokerite, paraffin, pentaerythrityl hydrogenated rosinate, pentaerythrityl tetraoctanoate, pentaerythrityl rosinate, pentaerythrityl tetraabietate, pentaerythrityl tetrabehenate, pentaerythrityl tetraoleate, pentaerythrityl tetrastearate, ophthalmic anhydride/glycerin/glycidyl decanoate copolymer, ophthalmic/trimellitic/glycols copolymer, polybutene, polybutylene terephthalate, polydipentene, polyethylene, polyisobutene, polyisoprene, polyvinyl butyral, polyvinyl laurate, propylene glycol dicaprylate, propylene glycol dicocoate, propylene glycol diisononanoate, propylene glycol dilaurate, propylene glycol dipelargonate, propylene glycol distearate, propylene glycol diundecanoate, PVP/eiconsene copolymer, PVP/hexadecene copolymer, rice bran wax, stearlkonium bentonite, stearalkonium hectorite, stearamide, stearamide DEA-distearate, stearamide DIBA-stearate, stearamide MEA-stearate, stearone, stearyl erucamide, stearyl stearate, stearyl stearoyl stearate, synthetic beeswax, synthetic wax, trihydroxystearin, triisononanoin, triisostearin, tri-isostearyl trilinoleate, trilaurin, trilinoleic acid, trilinolein, trimyristin, triolein, tripalmitin, tristearin, zinc laurate, zinc myristate, zinc neodecanoate, zinc rosinate, and mixtures thereof. Gelling agents used in vehicles may be natural gelling agents such as natural gums, starches, pectins, agar and gelatin, and may be based on polysaccharides or proteins Examples include but are not limited to guar gum, xanthum gum, alginic acid (E400), sodium alginate (E401), potassium alginate (E402), ammonium alginate (E403), calcium alginate (E404), polysaccharides from brown algae), agar (E406, a polysaccharide obtained from red seaweeds), carrageenan (E407, a polysaccharide obtained from red seaweeds), locust bean gum (E410, a natural gum from the seeds of the Carob tree), pectin (E440, a polysaccharide obtained from apple or citrus-fruit), and gelatin (E441, made by partial hydrolysis of animal collagen).

A composition as disclosed herein may optionally further comprise a surfactant. The surfactant may be an anionic surfactant, a cationic surfactant, an ampholytic surfactant, or a nonionic surfactant. Non-limiting examples of surfactants include polyethoxylates, fatty alcohols (e.g., ceteth-20 (a cetyl ether of polyethylene oxide having an average of about 20 ethylene oxide units) and other "BRIJ"™ nonionic surfactants available from ICI Americas, Inc. (Wilmington, Del.)), cocamidopropyl betaine, alkyl phenols, fatty acid esters of sorbitol, sorbitan, or polyoxyethylene sorbitan. Suitable anionic surfactants include ammonium lauryl sulfate and lauryl ether sulfosuccinate.

A composition as disclosed herein may optionally further comprise a silicone polymer, for example one or more than one polydimethylsiloxane polymer (Dow Corning 225 Silicone Fluid), dimethiconol fluid in dimethicone (Dow Corning 1403 Silicone Fluid), cyclomethicone and dimethicone copolyl (Dow Corning 3225C Silicone Fluid), silicone glycol (BASF 1066 DCG polyol), and combinations thereof.

A composition as disclosed herein may optionally further comprise one or more additives such as dyes, fragrances, pH adjusters, including basic pH adjusters such as ammonia, mono-, di- and tri-alkyl amines, mono-, di- and tri-alkanolamines, alkali metal and alkaline earth metal hydroxides (e.g., ammonia, sodium hydroxide, potassium hydroxide, lithium hydroxide, monoethanolamine, triethylamine, isopropylamine, diethanolamine and triethanolamine); acid pH adjusters such as mineral acids and polycarboxylic acids; vitamins such as vitamin A, vitamin E and vitamin C; polyamino acids and salts, such as ethylenediamine tetraacidic acid (EDTA), preservatives such as Germall plus and DMDM hydantoin, and sunscreens such as aminobenzoic acid, arobenzone, cinoxate, diioxybenzone, homosalate, menthyl anthranilate, octocrylene, octyl methoxycinnamate, octyl salicylate, oxybenzoate, padimate O, phenylbenzimidazole, sulfonic acid, sulisobenzone, titanium dioxide, trolamine salicylate and zinc oxide.

In certain non-limiting embodiments the composition may contain a cationic emulsifer selected from the group consisting of incroquat compounds such as (but not limited to) behenyltrimonium methosulfate in cetearyl alcohol (e.g., incroquat behenyl TMS and incroquat behenyl TMS 50 (Croda Inc., Edison, N.J.)), behenalkonium chloride and cetyl alcohol (e.g., Incroquat B-65 (Croda Inc., Edison, N.J.)), behenamido propyl ethyl dimonium ethosulfate and stearyl alcohol (Incroquat BES-35 S (Croda Inc., Edison, N.J.)), steralkonium chloride and cetearyl alcohol and PEG-40 Castor oil (e.g., Incroquat CR concentrate (Croda Inc., Edison, N.J.)), Incroquat CTC-30 (Croda Inc., Edison, N.J.), Incroquat DBM-90 (Croda Inc., Edison, N.J.), Incroquat O-50 (Croda Inc., Edison, N.J.), Incroquat S-DQ-25 (Croda Inc., Edison, N.J.), Incroquat BA-85 (Croda Inc., Edison, N.J.), Incroquat WG-85 (Croda Inc., Edison, N.J.), as well as distearyldimonium chloride (e.g., VARISOFT® TA 100 (Essen-Degussa, Germany)), palmitamidopropyltrimonium chloride (e.g., VARISOFT® PATC (Essen-Degussa, Germany)), and cetearyl alcohol (and) palmitamidopropyltrimonium chloride (e.g., TEGO® Care CE 40).

4.7 Methods of Use

Disclosed herein are methods of inhibiting the growth of a microbe in a personal care formulation, topical disinfectant, pesticide and/or disinfectant for food, comprising incorporating a composition, as described above, into said personal care formulation, topical disinfectant, pesticide and/or disinfectant for food. In certain non-limiting embodiments, the microbe, the growth of which is inhibited, is a bacterium or yeast or fungus, for example, but not limited to, *Staphylococcus aureus, Staphylococcus epidermidis, Enterococcus, Escherichia coli, Pseudomonas aeruginosa, Candida albicans*, and *Aspergillus niger*. In certain non-limiting embodiments, the personal care formulation, topical disinfectant, pesticide and/or disinfectant for food is an anionic formulation; in others, it is a cationic formulation. In certain non-limiting embodiments, growth is inhibited by at least about 10 percent or at least about 20 percent or at least about 30 percent or at least about 40 percent or at least about 50 percent. In certain non-limiting embodiments, the inhibition occurs over a period of up to about 3 months, or up to about 6 months, or up to about 12 months, or up to about 18 months, or up to about 24 months, or up to about 30 months.

5. EXAMPLE 1

Efficacy of Benzyl Alcohol and Botanical Extracts Against Various Pathogens in Cationic and Anionic Emulsions The formulations used in this study included BA combined with THC, 15 citrus fruit extract ("CT"), grapefruit seed extract ("GSE"), or W in an emulsion having the following formulation:

| Formulation A (Cationic emulsion) | |
|---|---|
| Ingredient | % w/w |
| Water | 75.5 |
| UcareJr 30 M | 0.24 |
| Incroquat TMS | 2.4 |
| Polawax NF | 2.4 |
| Petrolatum | 4.8 |
| Stearyl alcohol | 6.6 |
| Polyoxyl 40 stearate | 1.6 |
| Propylene glycol | 1.6 |
| Isopropyl myristate | 3.2 |
| Sorbitan oleate | 1.6 | pH 6.5

| Formulation B (Anionic emulsion) | |
|---|---|
| Ingredient | % w/w |
| Water | 78.0 |
| Propylene glycol | 2.0 |
| Mineral oil | 9.5 |
| Ceteareth 25 | 2.5 |
| Cetearyl Alcohol | 4.0 |
| Glyceryl stearate | 2.0 |
| Monoglyceryl citrate | 2.0 | pH 5.0

The testing method was based on the guidelines issued by the Cosmetics, Toiletries, and Fragrance Association, Inc. [CTFA, 2001] Briefly, 25 gms of emulsion containing 0.85% of various preservative was prepared. 0.9 gm aliquots of preservative containing emulsions were dispensed into several culture tubes. These were divided into various groups and inoculated with 0.1 ml of the test organism (bacteria, *Candida albicans* ($10^8$ cfu/ml) or *Aspergillus niger* ($10^7$ cfu/ml). After mixing, the tubes were incubated for 48 hours for bacteria t days for either *C. albicans* or *A. niger*. The cultures were then diluted serially with Drug Neutralizing Fluid (DNF) and 0.5 ml aliquots were plated on TSA and incubated for 24-48 hours (bacteria and *C. albicans* were incubated at 37° C. and *A. niger* at 30° C.). In the control group, the emulsion base without the preservatives was inoculated with each organism and processed similarly. The log 10 reduction in colony counts of the test group from the colony counts of control group was determined, and the results are shown in TABLES 1 and 2 below for cationic and anionic emulsions, respectively.

The preservatives in the final emulsions used for testing contains the following percent of each ingredient.

BA+THC+CT: BA (0.5%)+THC (0.05%)+CT (citrus extract 0.3%)

BA+THC+GSE: BA (0.5%)+THC (0.05%)+GSE (0.3%)

BA+THC+W: BA (0.5%)+THC (0.05%)+W (0.3%)

TABLE 1

| CATIONIC EMULSION* | | | | |
|---|---|---|---|---|
| | S. aureus | P. aeruginosa | C. albicans | A. niger |
| BA + THC + CT | 5.3 | 5.4 | 4.0 | 4.4 |
| BA + THC + GSE | 5.6 | 3.27 | 3.9 | 4.4 |
| BA + THC + W | 5.6 | 3.27 | 3.9 | 4.4 |

*log10 reduction in colony counts

TABLE 2

| ANIONIC EMULSION* | | | | |
|---|---|---|---|---|
| | S. aureus | P. aeruginosa | C. albicans | A. niger |
| BA + THC + CT | 4.0 | 5.3 | 5 | 0.57 |
| BA + THC + GSE | 3.1 | 5.0 | 4.0 | 0.2 |
| BA + THC + W | 3.1 | 5.0 | 4.0 | 0.61 |

*log10 reduction in colony counts
Conclusion: All the above groups do not show efficacy against *A. niger* in anionic emulsion.

6. EXAMPLE 2

Efficacy of Synergistic Combinations of BA, THC and Essential Oils Incorporated in an Anionic Emulsion Against *A. niger*

Various essential oils were used along with BA and THC and incorporated in anionic emulsion and tested against *A. niger*. Formulations comprising essential oil alone, at a concentration of 0.3% w/w with the essential oil at the same concentration combined with BA at 0.5% w/w and THC at 0.05% w/w (a concentration of cinnamon bark oil at a concentration of 0.1% w/w in combination with BA an THC was also tested). All formulations had an anionic emulsion base having the formula provided above. The testing method was the same as described for Example 1 except that 10' cfu *A. niger*/gm of anioninc emulsion was used and the incubation time was only 48 hours. The results are shown in TABLE 3, and indicate that of all the essential oils tested, cinnamon bark oil was the most effective against *A. niger* in the anionic emulsion formulation.

TABLE 3*†

EFFICACY AGAINST *A. NIGER* IN ANIONIC EMULSION

| active ingredients | log10 reduction in cfu |
|---|---|
| B | 0.5 |
| BA + THC + B | 0.90 |
| CL | 0.8 |
| BA + THC + CL | 1.11 |
| CB (0.3% w/w) | 0.88 |
| BA + THC + CB (0.3% w/w) | 5.78 |
| BA + THC + CB (0.1% w/w) | 3.28 |
| LG | 0.5 |
| BA + THC + LG | 0.83 |
| PS | 0.5 |
| BA + THC + PS | 0.90 |
| CU | 0.8 |
| BA + THC + CU | 1.03 |
| GG | 0.7 |
| BA + THC + GG | 1.14 |
| RM | 0.5 |
| BA + THC + RM | 0.85 |
| TH | 0.8 |
| BA + THC + TH | 1.2 |
| BA + THC | 0.21 |

*CL = Cinnamon leaf oil, CU = Curry leaf oil, GG = Galangal oil RM = Rosemary oil, LG = Lemongrass oil, B = Basil oil, PS = Pomegranate seed oil, CB = Cinnamon bark oil. TH = Thymol.
†The control growth ranged from $5 \times 10^6$ to $1 \times 10^7$ cfu/ml. Results are the average of nine samples in each group.

7. EXAMPLE 3

Since, as shown in Example 2, CB was found to be the most effective essential oil against *A. niger* in anionic formulations, combinations of lower concentration of CB (0.1%) alone with BA+THC were prepared. The odor of CB could be significantly masked by orange oil (OR) or rosemary oil (RM).

A stock solution was prepared containing the active ingredients and was then diluted in either a cationic or anionic test formulation, where the cationic formulation tested was Formulation A described in Example 1 and the anionic formulation tested was Formulation B described in Example 1:

Test formulations comprising the synthetic preservative methylparaben, at a concentration of 0.3% w/w, was used as a positive control.

The following method of testing for antimicrobial activity was used. 25 gms of emulsion containing 1-1.2% of various preservative was prepared. 0.9 gm aliquots of preservative containing emulsions were dispensed into several culture tubes. These were divided into various groups and inoculated with 0.1 ml of the test organism (bacteria, *Candida albicans* ($10^8$ cfu/ml) or *Aspergillus niger* ($10^7$ cfu/ml)). After mixing, the tubes were incubated for 48 hours for bacteria and for 7 days days for either *C. albicans* or *A. niger*. The cultures were then diluted serially with Drug Neutralizing Fluid (DNF) and 0.5 ml aliquots were plated on TSA and incubated for 24-48 hours (bacteria and *C. albicans* were incubated at 37° C. and *A. niger* at 30° C.). In the control group, the emulsion base without the preservatives was inoculated with each organism and processed similarly. The log 10 reduction in colony counts of the test group from the colony counts of control group was determined.

7.1 CB, with or without Phenyl Ethanol

The test cationic and anionic formulations contain 0.65% w/w of the following stock solution (percentages w/w):

| BATCB without PE | | |
|---|---|---|
| | Stock | Test |
| BA | 77 | 0.5 |
| THC | 7.7 | 0.05 |
| CB | 15.3 | 0.1 |

The test cationic and anionic formulations, contains 0.9% w/w of the following stock solution (percentages w/w):

| BATCB with PE | | |
|---|---|---|
| | Stock | Test |
| BA | 55.5 | 0.5 |
| THC | 5.6 | 0.05 |
| Phenyl ethanol | 27.8 | 0.25 |
| CB | 11.1 | 0.1 |

Cationic or anionic test formulations were then tested for antimicrobial activity, measured as log 10 reduction in colony forming units (cfu). The results are shown in TABLE 4.

TABLE 4

| log reduction from control growth | S. aureus | P. aeruginosa | C. albicans | A. niger |
|---|---|---|---|---|
| CBw/oPE anionic | 6.8 | 6.8 | 6.0 | 5.0 |
| CBw/oPE cationic | 7.0 | 7.0 | 5.8 | 5.0 |
| CB + PE anionic | 7.0 | 7.0 | 6.0 | 5.2 |
| CB + PE cationic | 7.0 | 7.0 | 5.8 | 5.2 |
| methyl paraben anionic | 0.12 | 0.11 | 4.31 | 2.88 |
| methyl paraben cationic | 1.9 | 2.1 | 4.25 | 4.16 |

7.2 CB, PE, RM with or without Zemea

A stock solution was diluted to constitute 1.1% w/w of the test formulation, "CB/PE/RM" (all values are % w/w):

| | Stock | Test |
|---|---|---|
| BA | 45.5 | 0.5 |
| THC | 4.6 | 0.05 |
| Phenyl ethanol | 22.7 | 0.25 |
| CB | 9.1 | 0.1 |
| RM | 18.1 | 0.2 |

A stock solution was diluted to constitute 1.3% w/w of the test formulation, "CB/PE/RM+Z", with the natural propanediol, Zemea® (all values are % w/w): Without Zemea is 1.1% and with Zemea is 1.3%

| | Stock | Test |
|---|---|---|
| BA | 38.5 | 0.5 |
| THC | 3.8 | 0.05 |
| Phenyl ethanol | 19.2 | 0.25 |

-continued

|     | Stock | Test |
|-----|-------|------|
| CB  | 7.7   | 0.1  |
| RM  | 15.4  | 0.2  |
| Zemea ® | 15.4 | 0.2 |

Cationic or anionic test formulations were then tested for antimicrobial activity, measured as log 10 reduction in colony forming units (cfu). The results are shown in TABLE 5.

TABLE 5

| log reduction from control growth | S. aureus | P. aeruginosa | C. albicans | A. niger |
|---|---|---|---|---|
| CB/PE/RM anionic | 7.0 | 7.0 | 6.2 | 5.3 |
| CB/PE/RM cationic | 7.0 | 7.0 | 6.0 | 5.3 |
| CB/PE/RM + Z anionic | 7.0 | 7.0 | 6.0 | 5.5 |
| CB/PE/RM + Z cationic | 7.0 | 7.0 | 6.0 | 5.3 |
| methyl paraben anionic | 0.12 | 0.11 | 4.31 | 2.88 |
| methyl paraben cationic | 1.9 | 2.1 | 4.25 | 4.16 |

7.3 CB, PE, OR

A stock solution was diluted to constitute 1.1% w/w of the test formulation, "CB/PE/OR" (all values are % w/w):

|     | Stock | Test |
|-----|-------|------|
| BA  | 45.5  | 0.5  |
| THC | 4.6   | 0.05 |
| Phenyl ethanol | 22.7 | 0.25 |
| CB  | 9.1   | 0.1  |
| OR  | 18.1  | 0.2  |

Cationic or anionic test formulations were then tested for antimicrobial activity, measured as log 10 reduction in colony forming units (cfu). The results are shown in TABLE 6.

TABLE 6

| log reduction from control growth | S. aureus | P. aeruginosa | P. albicans | A. niger |
|---|---|---|---|---|
| CB/PE/OR anionic | 7.0 | 7.0 | 6.0 | 5.3 |
| CB/PE/OR cationic | 7.0 | 7.0 | 6.0 | 5.2 |
| methyl paraben anionic | 0.12 | 0.11 | 4.31 | 2.88 |
| methyl paraben cationic | 1.9 | 2.1 | 4.25 | 4.16 |

7.4 without THC, CB

A stock solution was diluted to constitute 1.1% w/w of the test formulation, "GGTHOR" (all values are % w/w):

|     | Stock | Test |
|-----|-------|------|
| BA  | 45.6  | 0.5  |
| GG  | 9.1   | 0.1  |
| Phenyl ethanol | 18.1 | 0.2 |
| TH  | 9.1   | 0.1  |
| OR  | 18.1  | 0.2  |

A stock solution was diluted to constitute 1.0% w/w of the test formulation, "GGTHCL" where citral is CL (all values are % w/w):

|     | Stock | Test |
|-----|-------|------|
| BA  | 50    | 0.5  |
| GG  | 10    | 0.1  |
| Phenyl ethanol | 20 | 0.2 |
| TH  | 10    | 0.1  |
| CL  | 10    | 0.1  |

Cationic or anionic test formulations were then tested for antimicrobial activity, measured as log 10 reduction in colony forming units (cfu). The results are shown in TABLE 7.

TABLE 7

| log reduction from control growth | S. aureus | P. aeruginosa | C. albicans | A. niger |
|---|---|---|---|---|
| GGTHOR anionic | 6.0 | 6.0 | 5.0 | 5.5 |
| GGTHOR cationic | 6.0 | 6.0 | 4.5 | 5.5 |
| GGTHCL anionic | 6.0 | 6.0 | 5.0 | 5.5 |
| GGTHCL cationic | 6.0 | 6.0 | 4.5 | 5.3 |
| methyl paraben anionic | 0.12 | 0.11 | 4.31 | 2.88 |
| methyl paraben cationic | 1.9 | 2.1 | 4.25 | 4.16 |

7.5 Conclusions

Preservative blends containing a combination of BA, THC, and CB with or without Zemea® showed a broad spectrum of activity both in cationic and anionic emulsions. Orange oil and rosemary oil masked the odor of cinnamon oil when incorporated in the emulsion. Phenyl ethanol (PE) can be used as a solvent. Other preservative blends which were effective was mixture of Thymol+Galangal oil along with BA+ orange oil or citral which is an ingredient of orange oil (citral) and PE as the solvent.

Various publications are cited herein, the contents of which are hereby incorporated by reference in their entireties.

We claim:

1. An antimicrobial composition consisting essentially of:
   between about 0.1 and 0.8 percent weight/weight benzyl alcohol;
   between about 0.05 and 0.5 percent weight/weight phenyl alcohol;
   between about 0.01 and 0.1 percent weight/weight tetrahydrocurcuminoid, curcumin, or combinations thereof;
   between about 0.01 and 0.1 percent weight/weight cinnamon bark oil; and between about 0.1 and 0.3 percent weight/weight benzoic acid.

2. An antimicrobial composition consisting essentially of:
between about 0.1 and 0.8 percent weight/weight benzyl alcohol;
between about 0.05 and 0.5 percent weight/weight phenyl alcohol;
between about 0.01 and 0.1 percent weight/weight tetrahydrocurcuminoid, curcumin, or combinations thereof;
between about 0.01 and 0.1 percent weight/weight cinnamon bark oil;
between about 0.1 and 0.3 percent weight/weight benzoic acid;
between about 0.05 and 0.1 percent weight/weight thymol; and
between about 0.5 and 1 percent weight/weight of a botanical extract selected from the group consisting of grapefruit seed extract, calendula extract, and combinations thereof.

* * * * *